US008802852B2

(12) United States Patent
Gessner et al.

(10) Patent No.: US 8,802,852 B2
(45) Date of Patent: Aug. 12, 2014

(54) AZIDE SUBSTITUTED NAPHTHYLENE OR RYLENE IMIDE DERIVATIVES AND THEIR USE AS REAGENTS IN CLICK-REACTIONS

(71) Applicants: Thomas Gessner, Heidelberg (DE); Helmut Reichelt, Neustadt (DE); Ingo Münster, Böhl-lggelheim (DE); Martin Könemann, Mannheim (DE); Neil Gregory Pschirer, Mainz (DE); Jianqiang Qu, Shanghai (CN); Rüdiger Sens, Ludwigshafen (DE); Anja Schwögler, Mutterstadt (DE); Antonio Manetto, München (DE)

(72) Inventors: Thomas Gessner, Heidelberg (DE); Helmut Reichelt, Neustadt (DE); Ingo Münster, Böhl-lggelheim (DE); Martin Könemann, Mannheim (DE); Neil Gregory Pschirer, Mainz (DE); Jianqiang Qu, Shanghai (CN); Rüdiger Sens, Ludwigshafen (DE); Anja Schwögler, Mutterstadt (DE); Antonio Manetto, München (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/085,058

(22) Filed: Nov. 20, 2013

(65) Prior Publication Data
US 2014/0080220 A1   Mar. 20, 2014

Related U.S. Application Data

(60) Division of application No. 13/006,572, filed on Jan. 14, 2011, now Pat. No. 8,618,297, which is a continuation-in-part of application No. 12/180,071, filed on Jul. 25, 2008, now abandoned.

(51) Int. Cl.
*C07D 221/18* (2006.01)
*G01N 21/76* (2006.01)

(52) U.S. Cl.
USPC .............................. 546/38; 436/172

(58) Field of Classification Search
USPC .............................. 546/38; 436/172
See application file for complete search history.

(56) References Cited

U.S. PATENT DOCUMENTS

| 6,184,378 | B1 | 2/2001 | Bohm et al. |
| 6,486,319 | B1 | 11/2002 | Bohm et al. |
| 2007/0004919 | A1 | 1/2007 | Kohl et al. |
| 2007/0155968 | A1 | 7/2007 | Konemann et al. |
| 2008/0167467 | A1 | 7/2008 | Konemann et al. |
| 2010/0022021 | A1 | 1/2010 | Gessner et al. |
| 2010/0324293 | A1 | 12/2010 | Kohl et al. |

FOREIGN PATENT DOCUMENTS

| DE | 19547210 A1 | 6/1997 |
| DE | 10308940 A1 | 9/2004 |
| DE | 10308941 A1 | 9/2004 |
| WO | WO-01/16109 A1 | 3/2001 |
| WO | WO-03/101972 A1 | 12/2003 |
| WO | WO-2005/070895 A1 | 8/2005 |
| WO | WO-2005/117161 A2 | 12/2005 |
| WO | WO-2006/116736 A2 | 11/2006 |
| WO | WO-2006/117161 A2 | 11/2006 |
| WO | WO-2007/006717 A1 | 1/2007 |
| WO | WO-2007/054470 A1 | 5/2007 |
| WO | WO-2008/052775 A2 | 5/2008 |

OTHER PUBLICATIONS

Mullen, K.M., et al., "Toward Multistation Rotaxanes Using Metalloporphyrin Coordination Templating," J. Org. Chem, (2008), vol. 73, No. 9, pp. 3336-3350.

Ustinov et al., "A convenient 'click chemistry' approach to perylene diimide-oligonucleotide conjugates", ScieneDirect, vol. 64, pp. 1467-1473, 2008.

*Primary Examiner* — Charanjit Aulakh
(74) *Attorney, Agent, or Firm* — Drinker Biddle & Reath LLP

(57) ABSTRACT

Novel mono-azide substituted rylene-imide derivatives, their use in methods for the detection of analytes and reagents kits for the detection of analytes comprising said novel mono-azide substituted rylene-imide derivatives.

7 Claims, 1 Drawing Sheet

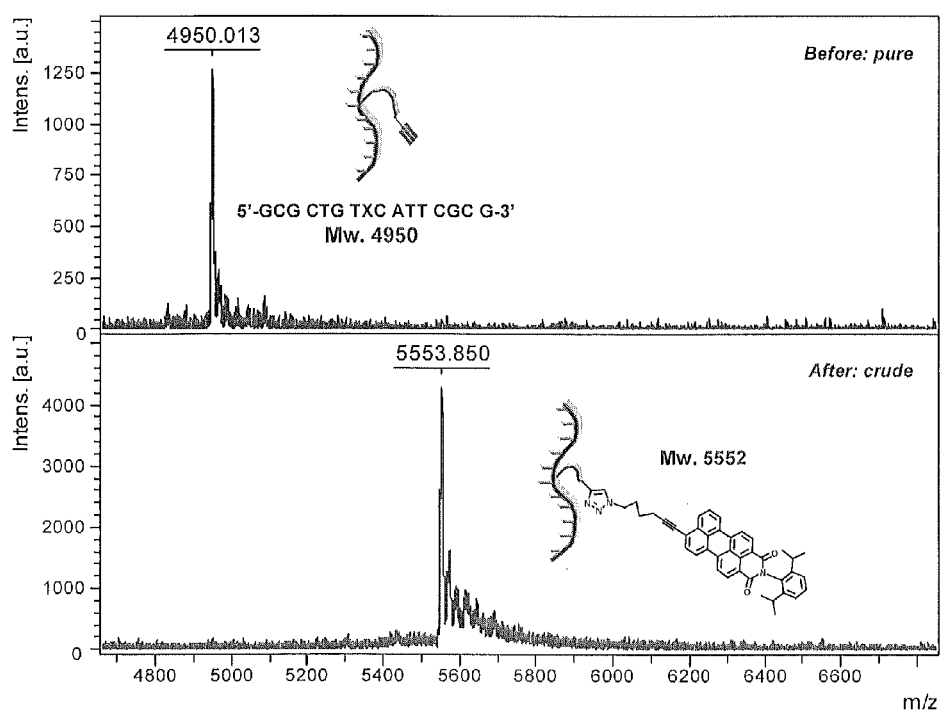

AZIDE SUBSTITUTED NAPHTHYLENE OR RYLENE IMIDE DERIVATIVES AND THEIR USE AS REAGENTS IN CLICK-REACTIONS

CROSS-REFERENCE TO RELATED APPLICATIONS

This application is a divisional of application Ser. No. 13/006,572, filed on Jan. 14, 2011, which is incorporated by reference herein in its entirety. Application Ser. No. 13/006,572 is a continuation-in-part of application Ser. No. 12/180,071 filed on Jul. 25, 2008 which is incorporated by reference in its entirety.

BACKGROUND OF THE INVENTION

The present invention relates to new mono-azide substituted naphthylene or rylene imide derivatives and their use as reagents in Click-reactions.

Perylene imides in general are known for their extraordinary thermal, chemical and photo-physical stability. They are widely used as pigments and dyestuffs, as photosensitizers in solar cells, in photovoltaic cells and in pigment lasers. Furthermore, they can be used as marker groups in processes for the detection of analytes, in particular in diagnostic or analytical processes for biological samples.

Their fluorescence excitation wavelengths above 500 nm are advantageous insofar as there are basically no signals deteriorating the measurement in this wavelength range arising from auto fluorescence of cells, biological tissues or biological fluids.

Click chemistry is a chemical philosophy introduced by Sharpless in 2001 and generally describes chemistry which is tailored to generate target substances quickly and reliably by joining small units together.

The well known [3+2]-cycloaddition of azides with terminal alkynes using a Cu-catalyst at ambient temperatures discovered concurrently and independently by the groups of Sharpless and Meldal is one of the best know examples of click-chemistry and is often referred to as the Click-reaction.

The difference between "click chemistry" and "click-reaction" is that the former is a chemical synthesis philosophy whereas the latter is a specific reaction and only one example of click-chemistry.

WO 2003/101972 describes reactions of terminal acetylenes and azides using Cu(I) as such or Cu(I) formed in situ by reduction of Cu(II) as a catalyst.

WO 2006/117,161 describes new labelling strategies for the sensitive detection of analytes in complex biological samples. One embodiment described therein is a method for detecting an analyte in a sample wherein
a sample is provided,
said sample is contacted with a functionalized compound comprising at least one functional group which is a first reaction partner for a click reaction under conditions wherein said compound forms an association product with the analyte to be detected,
the association product is contacted with a second reaction partner for a Click reaction under conditions where a Click reaction between the first and second reaction partner occurs, wherein the second reaction partner further comprises a marker group
and, finally,
said marker groups are detected. The Click reaction between an azide and an alkyne is mentioned as a preferred embodiment. Suitable marker groups mentioned are, e.g., fluorescent marker groups, hydrazones or oximes.

WO 2008/052775 relates to Click chemistry for the production of reporter molecules suitable for the detection of analytes, e.g. nucleic acids. According to this invention, reporter molecules comprising at least two different functional groups are provided which are selectively coupled to first and second reaction partners. Thus, a sequence specific detection of nucleic acids with high sensitivity is possible.

Neither perylene imides nor their derivatives are disclosed as reactants for the Click reaction.

In Tetrahedron 64, 1467-73 (2008) perylene diimide-oligonucleotide conjugates are disclosed, which are obtained by Huisgen [3+2] cycloaddition in water/DMSO using Cu(I) as catalyst. The perylene diimides used carry two azide groups attached to the imide nitrogen via a spacer. Due to the double substitution with azide groups at both nitrogen atoms of the imide groups, crosslinking and chain elongation reactions might occur, which makes the use of the bis-azides as marker reagent not preferable.

WO 2007/054470 discloses rylene derivatives and their use as photosensibilizer in solar cells. Perylene diimides are included in the compounds disclosed.

BRIEF DESCRIPTION OF THE INVENTION

It was an object of this invention to provide reactants for a Click chemistry reaction useful in the analysis of biological samples which carry a marker group easily detectable with high sensitivity. Detection should be preferably by optical means with e.g. laser spectroscopy or fluorescence spectroscopy with available equipment, i.e. at a wavelength used by commercially available spectrometers.

This object is achieved with new azide substituted rylene imide derivatives of formula I in accordance with claim 1.

Preferred embodiments are disclosed in the dependent claims.

Thus, the present invention relates to new azide-substituted naphthylene or rylene imide derivatives of the general formula I

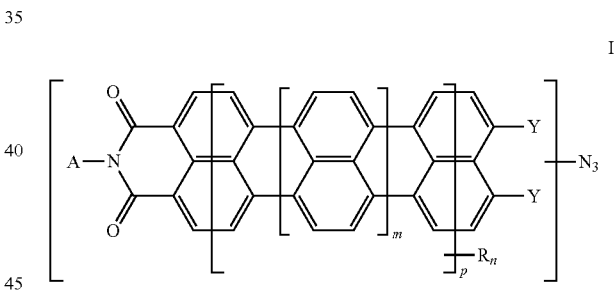

in which the variables are each defined as follows:
Y one of the two radicals is a radical of the formula (y1)

$$\text{-L-Z—R}^1 \tag{y1}$$

and the other radical in each case is hydrogen;
or both Y together form a six-membered ring to give a radical of the formula (y2)

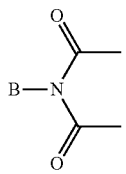

R are identical or different radicals:
aryloxy, arylthio, hetaryloxy or hetarylthio, to each of which may be fused further saturated or unsaturated 5- to 7-membered rings whose carbon skeleton may be interrupted by one or more —O—, —S—, —NR$^2$—, —N=CR$^2$—, —CO—, —SO— and/or —SO$_2$— moieties, where the entire ring system may be mono- or polysubstituted by the (i), (ii), (iii), (iv) and/or (v) radicals:

(i) $C_1$-$C_{30}$-alkyl whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties and which may be mono- or polysubstituted by: $C_1$-$C_{12}$-alkoxy, $C_1$-$C_8$-alkylthio, —C≡CR$^2$, —CR$^2$=CR$^2{}_2$, hydroxyl, mercapto, halogen, cyano, nitro, —NR$^7$R$^8$, —NR$^3$COR$^4$, —CONR$^3$R$^4$, —SO$_2$NR$^3$R$^4$, —COOR$^5$, —SO$_3$R$^5$, —PR$^5{}_2$, —POR$^5$R$^5$, (het)aryl and/or saturated or unsaturated $C_4$-$C_7$-cycloalkyl whose carbon skeleton may be interrupted by one or more —O—, —S—, —NR$^2$—, —N=CR$^2$—, —CR$^2$=CR$^2$—, —CO—, —SO— and/or —SO$_2$— moieties, where the (het)aryl and cycloalkyl radicals may each be mono- or polysubstituted by $C_1$-$C_{18}$-alkyl and/or the above radicals specified as substituents for alkyl;

(ii) $C_3$-$C_8$-cycloalkyl whose carbon skeleton may be interrupted by one or more —O—, —S—, —NR$^2$—, —N=CR$^2$—, —CR$^2$=CR$^2$—, —CO—, —SO— and/or —SO$_2$— moieties and to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^2$, —CR$^2$=CR$^2{}_2$, hydroxyl, mercapto, halogen, cyano, nitro, —NR$^7$R$^8$, —NR$^3$COR$^4$, —CONR$^3$R$^4$, —SO$_2$NR$^3$R$^4$, —COOR$^5$, —SO$_3$R$^5$, —PR$^5{}_2$ and/or —POR$^5$R$^5$;

(iii) aryl or hetaryl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by: $C_1$-$C_{18}$-alkyl, $C_1$-$C_{12}$-alkoxy, alkylthio, —C≡CR$^2$, —CR$^2$=CR$^2{}_2$, hydroxyl, mercapto, halogen, cyano, nitro, —NR$^7$R$^8$, —NR$^3$COR$^4$, —CONR$^3$R$^4$, —SO$_2$NR$^3$R$^4$, —COOR$^5$, —SO$_3$R$^5$, —PR$^5{}_2$, —POR$^5$R$^5$, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, $C_1$-$C_8$-alkylthio, hydroxyl, mercapto, halogen, cyano, nitro, —NR$^7$R$^8$, —NR$^3$COR$^4$, —CONR$^3$R$^4$, —SO$_2$NR$^3$R$^4$, —COOR$^5$, —SO$_3$R$^5$, —PR$^5{}_2$, —POR$^5$R$^5$;

(iv) a —U-aryl radical which may be mono- or polysubstituted by the above radicals specified as substituents for the aryl radicals (iii), where U is a —O—, —S—, —CO—, —SO— or —SO$_2$— moiety;

(v) $C_1$-$C_{12}$-alkoxy, $C_1$-$C_8$-alkylthio, —C≡CR$^2$, —CR$^2$=CR$^2{}_2$, hydroxyl, mercapto, halogen, cyano, nitro, —NR$^7$R$^8$, —NR$^3$COR$^4$, —CONR$^3$R$^4$, —SO$_2$NR$^3$R$^4$, —COOR$^5$, —SO$_3$R$^5$, —PR$^5{}_2$ and/or —POR$^5$R$^5$;

(vi) E-D-SO$_3{}^-$, D is selected from the group of residues as depicted under (ii) and (iii), whereby the counterion of the anion (—SO$_3{}^-$) respectively cation is selected from the group consisting of metal ion and quarternary ammonium ions, L is a chemical bond
  or an arylene or hetarylene radical, bonded to the rylene skeleton directly or via ethenylene or ethynylene, of the formulae —Ar—

—Ar-E-Ar— in which the (het)arylene radicals Ar may be the same or different, may comprise heteroatoms as ring atoms and/or may have fused saturated or unsaturated 5- to 7-membered rings which may likewise comprise heteroatoms, where the entire ring system may be mono- or polysubstituted by phenyl, $C_1$-$C_{12}$-alkyl, $C_1$-$C_{12}$-alkoxy, $C_1$-$C_{12}$-alkylthio and/or —NR$^3$R$^4$;

E is a chemical bond or an —O—, —S—, —NR$^2$—, —CR$^2$=CR$^2$— or $C_1$-$C_6$-alkylene moiety;

Z is —O— or —S— or a carbon-carbon single, double or triple bond, provided that L and Z are not simultaneously a chemical bond;

R$^1$ is one of the alkyl radicals (i) or (het)aryl radicals (iii) specified as substituents for the R radicals;

A, B are the same or different and independent of each other hydrogen;
  $C_1$-$C_{30}$-alkyl whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties and which may be mono- or polysubstituted by the (ii), (iii), (iv) and/or (v) radicals specified as substituents for the R radicals;
  $C_3$-$C_8$-cycloalkyl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by the (i), (ii), (iii), (iv) and/or (v) radicals specified as substituents for the R radicals;
  aryl or hetaryl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by the (i), (ii), (iii), (iv), (v) radicals specified as substituents for the R radicals, and/or aryl- and/or hetarylazo, each of which may be substituted by $C_1$-$C_{10}$-alkyl, $C_1$-$C_6$-alkoxy and/or cyano;
  E-D-SO$_3{}^-$, D is selected from the group of residues as depicted under (ii) and (iii), whereby the counterion of the anion (—SO$_3{}^-$) respectively cation is selected from the group consisting of metal ion and quarternary ammonium ions, R$^2$ is hydrogen or $C_1$-$C_{18}$-alkyl, where the R$^2$ radicals may be the same or different when they occur more than once;

R$^3$, R$^4$ are each independently:
  hydrogen;
  $C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^5$;
  aryl or hetaryl to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by $C_1$-$C_{12}$-alkyl and/or the above radicals specified as substituents for alkyl;
where the $R^3$ radicals may be the same or different when they occur more than once;
$R^5$ is hydrogen,
$C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^6$;
aryl or hetaryl to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by $C_1$-$C_{12}$-alkyl and/or the above radicals specified as substituents for alkyl,
where the $R^5$ radicals may be the same or different when they occur more than once;
$R^6$ is $C_1$-$C_{18}$-alkyl;
$R^7$, $R^8$ are each $C_1$-$C_{30}$-alkyl whose carbon chain may be interrupted by one or more —O—, —S—, —N=CR$^2$—, —C≡C—, —CR$^2$=CR$^2$—, —CO—, —SO— and/or —SO$_2$— moieties and which may be mono- or polysubstituted by: $C_1$-$C_{12}$-alkoxy, $C_1$-$C_8$-alkylthio, —C≡CR$^2$, —CR$^2$=CR$^2{}_2$, hydroxyl, —NR$^3$R$^4$, —NR$^3$COR$^4$, (het) aryl and/or saturated or unsaturated $C_4$-$C_7$-cycloalkyl whose carbon skeleton may be interrupted by one or more —O—, —S—, —NR$^2$—, —N=CR$^2$— and/or —CR$^2$=CR$^2$ moieties, where the (het)aryl and cycloalkyl radicals may each be mono- or polysubstituted by $C_1$-$C_{18}$-alkyl and/or the above radicals specified as substituents for alkyl;
aryl or hetaryl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^2$, —CR$^2$=CR$^2{}_2$, hydroxyl, —NR$^3$R$^4$, —NR$^3$COR$^4$, (het) aryl, (het)aryloxy and/or (het)arylthio, where the (het) aryl radicals may in each case be mono- or polysubstituted by $C_1$-$C_{18}$-alkyl, $C_1$-$C_{12}$-alkoxy, hydroxyl, —NR$^3$R$^4$ and/or —NR$^3$COR$^4$;
joined to the nitrogen atom to form a saturated or unsaturated, 5- to 7-membered ring whose carbon chain may be interrupted by one or more —O—, —S— and/or —NR$^2$— moieties, to which may be fused one or two unsaturated or saturated 4- to 8-membered rings whose carbon chain may likewise be interrupted by these moieties and/or —N=, where the entire ring system may be mono- or polysubstituted by $C_1$-$C_{24}$-alkyl which may be substituted by $C_1$-$C_{18}$-alkoxy, $C_1$-$C_{18}$-alkylthio and/or —NR$^3$R$^4$, (het)aryl which may be mono- or polysubstituted by $C_1$-$C_{18}$-alkyl and/or the above radicals specified as substituents for alkyl, $C_1$-$C_{18}$-alkoxy, $C_1$-$C_{18}$-alkylthio and/or —NR$^3$R$^4$;
m is 0 or 1;
n is an integer in the range of from 0 to 6, and
p is 0 or 1
and their use as reactants in Click reactions.

A further object of the invention is the use of the new mono-azide substituted naphthylene or rylene imides as reactants in a click reaction.

A further object of the invention is a method for detection an analyte in a sample using a click reaction with the new mono-azide substituted naphthylene or rylene imides as one of the reactants.

BRIEF DESCRIPTION OF THE FIGURE

FIG. 1 illustrates the results according to Example 6.

DETAILED DESCRIPTION OF THE INVENTION

Preferred embodiments of the invention can be taken from the dependent claims and the detailed specification and examples hereinafter.

Preferred naphthylene or rylene imide derivatives of formula I are the following

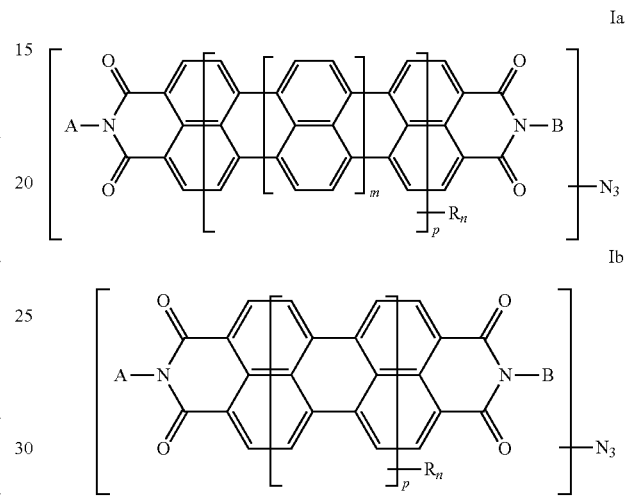

wherein A, B and R have the meaning defined above. In some applications compounds of formula Ia have proved particularly advantageous, where A and B are, independently of the other, aryl groups, preferably substituted with alkyl groups or halogen.

In another preferred group of compounds of formula Ia A, and B are independently of each other alkyl groups, optionally substituted with terminal hydroxyl, halogen or sulfonyl groups, m is 0 or 1 and R has the meaning defined above.

According to a preferred embodiment, R in compounds of formula Ia or Ib is an aryloxy group, where the aryl ring can be substituted by the substituents as defined hereinbefore, preferably by $C_1$-$C_{12}$-alkyl (whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties), halogen, sulfonyl or hydroxyl and n has a value of from 0 to 6, preferably of from 0 to 4 and particularly preferred of from 0 to 2 in those cases where m is 0.

In one embodiment of the invention, R is E-D-SO$_3^-$, C is selected from the group of residues as depicted under (ii) and (iii),
preferably E is a chemical bond or —O—,
preferably D is an aryl, more preferably phenyl,
whereby the counterion of the anion (—SO$_3^-$) respectively cation is selected from the group consisting of metal ion and quarternary ammonium ions,
preferably alkali and earth alkali metals, more preferably Na, or ammonium or tetraalkyl-ammonium ions.

In a further embodiment, preferably when R is E-D-SO$_3^-$, n has a value of from 1 to 6, preferably of from 1 to 4 and particularly preferred of from 1 or 2 and m is 0

The preferred compounds of formulae Ia and Ib are naphthylene or rylene bisimides; the invention also provides novel naphthylene or rylene monoimides of formula Ic

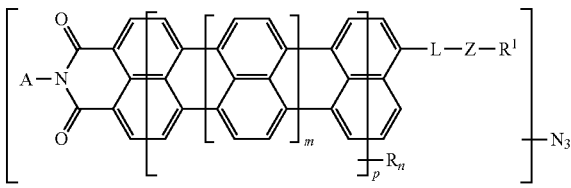

Preferably, when L is a chemical bond, Z is —O— or —S— and R¹ is as defined above. When Z is a chemical bond, L is not at the same time a chemical bond. Particularly preferred compounds of formula Ic are compounds where R¹ is an alkyl group or an aryloxy group, where the alkyl chain or the aryl ring can be substituted by a substituent as defined hereinbefore for R¹, preferably by an alkyl group.

The azide substitutent in the compounds of formula I can be attached to the aromatic rings of the system, to one of the possible substituents at these ring systems or can be attached to the imide nitrogen atom through a substituent as defined hereinbefore. Generally, the azide functionality is in a terminal position, either at the rylene structure itself or as a terminal group of one of the substituents as defined hereinbefore.

Processes and methods for the introduction of azide substituents are known to the man skilled in the art and thus there are no detailed explanations necessary here.

Only for illustrative purposes reference is made to the conversion of terminal hydroxy groups to azide groups with sodium azide with a suitable catalyst under usual conditions known to the man skilled in the art.

For exemplary purposes, the reaction can be outlined as follows:

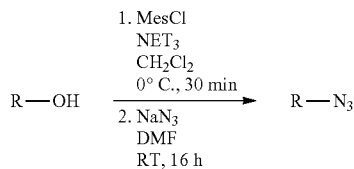

or, alternatively

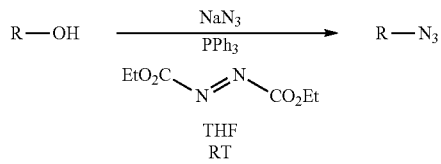

The rylene-imide derivatives I according to the invention may be unsubstituted at the end of the molecule opposite to the imide group (both Y radicals hydrogen) or be substituted in the peri-position by a (thio)ether radical (y1)

 (y1)

(the second Y radical is accordingly hydrogen) or be present as the imide (y2)

(y2)

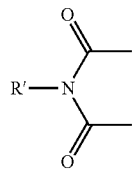

(the Y radicals here are joined together to form a six-membered ring).

In the (thio)ether radicals (y1), the (thio)ether function is bonded to the rylene skeleton via a bridging member L.

The bridging member L may be a chemical bond, i.e. the (thio)ether group is bonded directly to the rylene skeleton, or a (het)arylene radical, bonded to the rylene skeleton directly or via ethenylene or ethynylene, of the formulae —Ar—

—Ar-E-Ar—

The (het)arylene radicals Ar may comprise heteroatoms as ring atoms and/or fused saturated or unsaturated 5- to 7-membered rings which may likewise comprise heteroatoms. When they are fused ring systems Ar, the bonds to the rylene skeleton and to the functional group may both start from the same ring or from different rings. The whole ring system may additionally be mono- or polysubstituted by phenyl, $C_1$-$C_{12}$-alkyl, $C_1$-$C_{12}$-alkoxy, $C_1$-$C_{12}$-alkylthio and/or —NR³R⁴, preference being given to $C_1$-$C_{12}$-alkyl, $C_1$-$C_{12}$-alkoxy and/or —NR³R⁴ as substituents.

When the bridging member L comprises two (het)arylene radicals Ar, they are preferably the same, but may also be different. The two Ar radicals may be bonded directly to one another or joined together via an —O—, —S—, —NR²—, —C≡C—, —CR²=CR²— or $C_1$-$C_6$-alkylene moiety. The bonding member E is preferably a chemical bond or an —O—, —S—, —NR²— or —C≡C— moiety.

Examples of suitable bridging members L include:
1,4-, 1,3- and 1,2-phenylene, 1,4- and 1,8-naphthylene, 1,4- and 2,3-pyrrylene, 2,5-, 2,4- and 2,3-thienylene, 2,5-, 2,4- and 2,3-furanylene, 2,3-, 2,4-, 2,5-, 2,6-, 3,4- and 3,5-pyridinylene, 2,3-, 2,5-, 2,6-, 3,7-, 4,8-, 5,8- and 6,7-quinolinylene, 2,7-, 3,6-, 4,5-, 2,6-, 3,7-, 4,7- and 4,8-isoquinolinylene, 4,4'-, 3,3'- and 2,2'-biphenylene, 3,3'- and 2,2'-bithienylene, 1,4-[2,5-di(tert-butyl)]phenylene, 1,4-(2,5-dihexyl)phenylene, 1,4-[2,5-di(tert-octyl)]phenylene, 1,4-(2,5-didodecyl)phenylene, 1,4-[2,5-di(2-dodecyl)]phenylene, 4,4'-di(2,2',6,6'-tetramethyl)phenylene, 4,4'-di(2,2',6,6'-tetraethyl)phenylene, 4,4'-di(2,2',6,6'-tetraisopropyl)phenylene, 4,4'-di(2,2',6,6'-tetrahexyl)phenylene, 4,4'-di[2,2',6,6'-tetra(2-hexyl)]phenylene, 4,4'-di[2,2',6,6'-tetra(tert-octyl)]phenylene, 4,4'-di(2,2',6,6'-tetradodecyl)phenylene and 4,4'-di[2,2',6,6'-tetra(2-dodecyl)]phenylene, and also

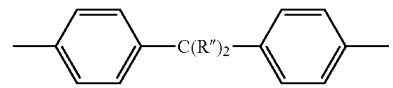

where R" is hydrogen, methyl, ethyl or phenyl.

Very particularly preferred bridging members L are a chemical bond, 1,4-phenylene and 4,4'-di(2,2',6,6'-tetramethyl)phenylene.

For the (thio)ether radical (y1), particularly preferred bridging members L are a chemical bond, 1,4-phenylene and 2,5-thienylene. A very particularly preferred bridging member L is the chemical bond.

The R¹ radical in the (thio)ether radical (y1) may be one of the alkyl radicals (i) or (het)aryl radicals (iii) mentioned at the outset as substituents in the definition of the variables R.

R¹ is preferably:
$C_1$-$C_{30}$-alkyl whose carbon chain may be interrupted by one or more —O—, —S— and/or —NR²— moieties and which may be mono- or polysubstituted by: $C_1$-$C_{12}$-alkoxy, hydroxyl and/or aryl which may be mono- or polysubstituted by $C_1$-$C_{18}$-alkyl or $C_1$-$C_6$-alkoxy;

phenyl which may be mono- or polysubstituted by: $C_1$-$C_{18}$-alkyl, $C_1$-$C_{12}$-alkoxy, $C_1$-$C_6$-alkylthio, —$NR^3R^4$ and/or phenoxy and/or phenylthio, each of which may be mono- or polysubstituted by $C_1$-$C_{18}$-alkyl, $C_1$-$C_{12}$-alkoxy, $C_1$-$C_6$-alkylthio and/or —$NR^3R^4$.

Examples of particularly preferred (y1) radicals are: phenoxy, phenylthio, naphthyloxy and/or naphthylthio, each of which may be mono- or polysubstituted by $C_4$-$C_{18}$-alkyl, $C_1$-$C_{18}$-alkoxy and/or —$NR^3R^4$.

In the imide radicals A and B, may be the same or different and, in addition to hydrogen, may be the alkyl radicals (i), cycloalkyl radicals (ii) or (het)aryl radicals (iii) defined at the outset.

A and B are preferably defined as follows:

$C_6$-$C_{30}$-alkyl whose carbon chain may be interrupted by one or more —O—, —S— and/or —$NR^2$— moieties and which may be mono- or polysubstituted by: $C_1$-$C_6$-alkoxy, $C_1$-$C_6$-alkylthio, —$NR^7R^8$ and/or aryl which may be mono- or polysubstituted by $C_1$-$C_{18}$-alkyl or $C_1$-$C_6$-alkoxy, particular preference being given to $C_6$-$C_{30}$-alkyl which is substituted in the ω-position by —$NR^7R^8$;

(het)aryl, especially phenyl, naphthyl, pyridyl or pyrimidyl, in particular phenyl, each of which may be mono- or polysubstituted by: $C_1$-$C_{18}$-alkyl, $C_1$-$C_6$-alkoxy, halogen, cyano, nitro, —$NR^7R^8$, —$CONR^3R^4$, —$SO_2NR^3R^4$ and/or phenoxy, phenylthio, phenylazo and/or naphthylazo, each of which may be substituted by $C_1$-$C_{10}$-alkyl, $C_1$-$C_6$-alkoxy and/or cyano.

Most preferably, A or B is a phenyl radical which is mono- or polysubstituted by $C_1$-$C_{18}$-alkyl or —$NR^7R^8$.

In one embodiment of the invention, A is E-D-$SO_3^-$, D is selected from the group of residues as depicted under (ii) and (iii), preferably E is a chemical bond or —O—, preferably D is an alkyl, more preferably ethyl, whereby the counterion of the anion (—$SO_3^-$) respectively cation is selected from the group consisting of metal ion and quarternary ammonium ions, preferably alkali and earth alkali metals, more preferably Na, or ammonium or tetraalkyl-ammonium ions.

In one embodiment of the invention, in case A is E-D-$SO_3^-$, p, m and n are 0.

The $R^3$ and $R^3$ radicals are each as defined at the outset. They are preferably each independently:

hydrogen;

$C_1$-$C_{18}$-alkyl which may be mono- or polysubstituted by $C_1$-$C_6$-alkoxy, hydroxyl, halogen and/or cyano;

aryl or hetaryl, each of which may be mono- or polysubstituted by $C_1$-$C_6$-alkyl and/or the above radicals mentioned as substituents for alkyl.

Particularly suitable substituents are the alkyl radicals and in particular the amino groups —$NR^7R^8$ The definition of the $R^7$ and $R^8$ radicals is likewise given at the outset. They are preferably each independently:

$C_1$-$C_{30}$-alkyl whose carbon chain may be interrupted by one or more —O—, —S—, —$NR^2$—, —N=$CR^2$—, —C≡C— and/or —$CR^2$=$CR^2$— moieties and which may be mono- or polysubstituted by: $C_1$-$C_{12}$-alkoxy, $C_1$-$C_8$-alkylthio, —C≡$CR^2$, —$CR^2$=$CR^2{}_2$, hydroxyl, —$NR^3R^4$, —$NR^3COR^4$ and/or (het)aryl which may be mono- or polysubstituted by $C_1$-$C_{18}$-alkyl and/or the above radicals mentioned as substituents for alkyl;

aryl or hetaryl, to which may be fused further saturated or unsaturated 5- to 7-membered rings whose carbon skeleton may be interrupted by one or more —O—, —S—, —$NR^2$—, —N=$CR^2$—, —$CR^2$=$CR^2$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^2$, —$CR^2$=$CR^2{}_2$, hydroxyl, —$NR^3R^4$, —$NR^3COR^4$, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, hydroxyl, —$NR^3R^4$ and/or —$NR^3COR^4$;

joined to the nitrogen atom to give a piperidyl, pyrrolidinyl, dibenzopyrryl, dibenzo-1,4-oxiranyl, dibenzo-1,4-thiazinyl, dibenzo-1,4-pyrazyl or dibenzopiperidyl ring system, each of which may be mono- or polysubstituted by $C_1$-$C_{24}$-alkyl which may be substituted by $C_1$-$C_{18}$-alkoxy, $C_1$-$C_{18}$-alkylthio and/or —$NR^3R^4$.

The amino groups —$NR^7R^8$ are preferably di(het)arylamino groups or cyclic amino groups. Particular preference is given to diphenylamino groups in which the phenyl radicals may be unsubstituted or may have the above substituents, especially the alkyl radicals, preferably in the p-position.

Preferred substitution patterns for the phenyl radicals A and/or B are ortho,ortho'-disubstitution (for example alkyl radicals with a secondary carbon atom in the 1-position) and para-substitution (for example alkyl radicals having a tertiary carbon atom in the 1-position and at least 5 carbon atoms or amino groups —$NR^7R^8$).

Examples of particularly preferred radicals A and/or B are:

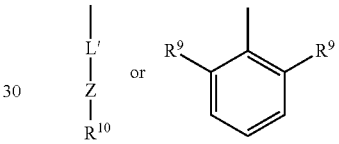

where the variables are each defined as follows:

$R^9$ is $C_3$-$C_8$-alkyl with a secondary carbon atom in the 1-position;

$R^{10}$ is phenyl when L' is a chemical bond;

$C_4$-$C_{18}$-alkyl when L' is 1,4-phenylene or a chemical bond

L' is a chemical bond, 1,4-phenylene or 2,5-thienylene;

Z is —O— or —S— or a carbon-carbon single, double or triple bond, provided that L' and Z are not simultaneously a chemical bond.

Very particularly preferred A and/or B radicals are the diphenylaminophenylene radicals.

The naphthylene or rylene derivatives I are preferably additionally substituted in the rylene skeleton. Preference is given to tetrasubstitution in the 1,6,7,12-position in the perylene derivatives and 1,6,9,14-position in the terrylene derivatives. In the perylene derivatives, disubstitution in the 1,6- and/or 1,7-position is also possible. The counting here always begins at the end of the molecule with the imino radical with substituent A.

In general, the rylene derivatives I are present in the form of mixtures of products with a different degree of substitution, in which the tetrasubstituted, or disubstituted products make up the main constituent. Since the substituents are typically introduced into the rylene skeleton by nucleophilic substitution of halogenated, especially brominated, rylene derivatives I or correspondingly halogenated precursors, the rylene derivatives I may still comprise traces of halogen which, if desired, can be removed by transition metal-catalyzed reductive or base-induced dehalogenation.

Suitable substituents are especially the (het)aryloxy and (het)arylthio radicals R defined at the outset. Particularly suitable substituents are phenoxy, thiophenoxy, pyridyloxy, pyrimidyloxy, pyridylthio and pyrimidylthio radicals. The R radicals may correspond to radicals of the formula (y2).

Preferred R radicals are phenoxy or thiophenoxy radicals, each of which may be mono- or polysubstituted by identical or different (i), (ii), (iii), (iv) and/or (v) radicals:

(i) $C_1$-$C_{30}$-alkyl whose carbon chain may be interrupted by one or more —O—, —S—, —NR$^2$—, —C≡C—, —CR$^2$=CR$^2$— and/or —CO— and/or —SO$_2$— moieties and which may be mono- or polysubstituted by: $C_1$-$C_{12}$-alkoxy, hydroxyl, halogen, cyano, and/or aryl which may be mono- or polysubstituted by $C_1$-$C_{18}$-alkyl or $C_1$-$C_6$-alkoxy;

(ii) $C_3$-$C_8$-cycloalkyl whose carbon skeleton may be interrupted by one or more —O—, —S—, —NR$^2$—, —N=CR$^2$—, —CR$^2$=CR$^2$— and/or —CO— moieties and which may be mono- or polysubstituted by: $C_1$-$C_{18}$-alkyl, $C_1$-$C_{12}$-alkoxy and/or $C_1$-$C_6$-alkylthio;

(iii) aryl or hetaryl, to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by: $C_1$-$C_{18}$-alkyl, $C_1$-$C_{12}$-alkoxy, —C=CR$^2{}_2$, —CR$^2$=CR$^2{}_2$, hydroxyl, halogen, cyano, —NR$^7$R$^8$, —NR$^3$COR$^4$, —CONR$^3$R$^4$, —SO$_2$NR$^3$R$^4$, —COOR$^5$ and/or —SO$_3$R$^5$, (het)aryl, (het)aryloxy and/or (het)arylthio, where the (het)aryl radicals may each be mono- or polysubstituted by $C_1$-$C_{18}$-alkyl, $C_1$-$C_{15}$-alkoxy and/or cyano;

(v) $C_1$-$C_{12}$-alkoxy, $C_1$-$C_6$-alkylthio, —C≡CR$^2$, —CR$^2$=CR$^2{}_2$, hydroxyl, mercapto, halogen, cyano, nitro, —NR$^7$R$^8$, —NR$^3$COR$^4$, —CONR$^3$R$^4$, —SO$_2$NR$^3$R$^4$, —COOR$^5$ or —SO$_3$R$^5$.

(vi) E-D-SO$_3^-$, C is selected from the group of residues as depicted under (ii) and (iii), whereby the counterion of the anion (—SO$_3^-$) respectively cation is selected from the group consisting of metal ion and quarternary ammonium ions, The (thio)phenoxy radicals R may be unsubstituted or monosubstituted in the ortho-, meta- or preferably para-position. They may also be di-, tri-, tetra- or pentasubstituted, all substitution patterns being conceivable.

Particularly preferred R radicals are ortho,ortho'-disubstituted (thio)phenoxy radicals of the formula —Z—[phenyl ring with R" in both ortho positions and R'" in both meta positions and R'" in para position].

The R" radicals in the two ortho-positions may be the same or different, but they are preferably the same.

The (thio)phenoxy radicals R may also be substituted in one, two or all three further ring positions by identical or nonidentical R'" radicals other than hydrogen.

The (thio)phenoxy radicals R are preferably substituted only in the ortho- and ortho'-position or additionally in the para-position.

In one embodiment of the invention, R is E-D-SO$_3^-$, D is selected from the group of residues as depicted under (ii) and (iii),
preferably E is a chemical bond or —O—,
preferably D is an aryl, more preferably phenyl,
whereby the counterion of the anion (—SO$_3^-$) respectively cation is selected from the group consisting of metal ion and quarternary ammonium ions,
preferably alkali and earth alkali metals, more preferably Na, or ammonium or tetraalkyl-ammonium ions.

In particular, the variables in the above mentioned formula are defined as follows:
Z is —O— or —S— or a carbon-carbon single, double or triple bond, preferably —O—;

R" are identical or different radicals:
(i) $C_1$-$C_{18}$-alkyl whose carbon chain may be interrupted by one or more —O—, —S—, —NR$^2$— and/or —CO— moieties and which may be mono- or polysubstituted by $C_1$-$C_{12}$-alkoxy, hydroxyl and/or halogen, where at most one of the R" radicals may have a tertiary carbon atom in the 1-position;
(ii) $C_3$-$C_8$-cycloalkyl which does not comprise a tertiary carbon atom in the 1-position and may be mono- or polysubstituted by $C_1$-$C_{18}$-alkyl and/or $C_1$-$C_{12}$-alkoxy, where at most one of the R" radicals may have a tertiary carbon atom in the 1-position;
(iii) aryl or hetaryl, each of which may be mono- or polysubstituted by $C_1$-$C_{18}$-alkyl, $C_1$-$C_{12}$-alkoxy, hydroxyl and/or halogen;
(iv) a —U-aryl radical which may be mono- or polysubstituted by the above radicals specified as substituents for the aryl radicals (iii), where U is an —O—, —S— or —NR$^2$— moiety;
(v) $C_1$-$C_{12}$-alkoxy, hydroxyl, halogen or cyano;

R'" are identical or different radicals:
hydrogen;
one of the (i), (ii), (iii), (iv) and (v) radicals mentioned for R", preferably $C_4$-$C_{18}$-alkyl radicals which comprise a tertiary carbon atom in the 1-position or whose carbon chain may be interrupted singly or multiply by —O—, —S— and/or —NR$^2$— and/or which may be mono- or polysubstituted by $C_1$-$C_{12}$-alkoxy, $C_1$-$C_{12}$-alkylthio and/or —NR$^3$R$^4$;

$R^2$ is hydrogen or $C_1$-$C_6$-alkyl.

Specific examples of particularly preferred (thio)phenoxy radicals include:
2,6-dimethylphenoxy, 2,6-diethylphenoxy, 2,6-diisopropylphenoxy, 2,6-di(2-butyl)-phenoxy, 2,6-di(n-butyl)phenoxy, 2,6-di(2-hexyl)phenoxy, 2,6-di(n-hexyl)phenoxy, 2,6-di(2-dodecyl)phenoxy, 2,6-di(n-dodecyl)phenoxy, 2,6-dicyclohexylphenoxy, 2,6-di-methyl-4-(n-butyl)phenoxy, 2,6-di-ethyl-4-(n-butyl)phenoxy, 2,6-diisopropyl-4-(n-butyl)-phenoxy, 2,6-di(2-butyl)-4-(n-butyl)phenoxy, 2,4,6-tri(n-butyl)phenoxy, 2,6-di(2-hexyl)-4-(n-butyl)phenoxy, 2,6-di(n-hexyl)-4-(n-butyl)phenoxy, 2,6-di(2-dodecyl)-4-(n-butyl)-phenoxy, 2,6-di(n-dodecyl)-4-(n-butyl)phenoxy, 2,6-dicyclohexyl-4-(n-butyl)phenoxy, 2,6-dimethyl-4-(n-nonyl)phenoxy, 2,6-diethyl-4-(n-nonyl)phenoxy, 2,6-diisopropyl-4-(n-nonyl)phenoxy, 2,6-di(2-butyl)-4-(n-nonyl)phenoxy, 2,6-di(2-butyl)-4-(n-nonyl)phenoxy, 2,6-di(2-hexyl)-4-(n-nonyl)phenoxy, 2,6-di(n-hexyl)-4-(n-nonyl)phenoxy, 2,6-di(2-dodecyl)-4-(n-nonyl)phenoxy, 2,6-di(n-dodecyl)-4-(n-nonyl)phenoxy, 2,6-dicyclohexyl-4-(n-nonyl)phenoxy, 2,6-dimethyl-4-(n-octadecyl)phenoxy, 2,6-diethyl-4-(n-octadecyl)-phenoxy, 2,6-diisopropyl-4-(n-octadecyl)phenoxy, 2,6-di(2-butyl)-4-(n-octadecyl)phen-oxy, 2,6-di(2-butyl)-4-(n-octadecyl)phenoxy, 2,6-di(2-hexyl)-4-(n-octadecyl)phenoxy, 2,6-di(n-hexyl)-4-(n-octadecyl) phenoxy, 2,6-di(2-dodecyl)-4-(n-octadecyl)phenoxy, 2,6-di(n-dodecyl)-4-(n-octadecyl)phenoxy, 2,6-dicyclohexyl-4-(n-octadecyl)phenoxy, 2,6-dimethyl-4-(tert-butyl)phenoxy, 2,6-diethyl-4-(tert-butyl)phenoxy, 2,6-diisopropyl-4-(tert-butyl)phenoxy, 2,6-di(2-butyl)-4-(tert-butyl)phenoxy, 2,6-di-(n-butyl)-4-(tert-butyl)phenoxy, 2,6-di(2-hexyl)-4-(tert-butyl)phenoxy, 2,6-di(n-hexyl)-4-(tert-butyl)-phenoxy, 2,6-di(2-dodecyl)-4-(tert-butyl)phenoxy, 2,6-di(n-dodecyl)-4-(tert-butyl)-phenoxy, 2,6-dicyclohexyl-4-(tert-butyl)phenoxy, 2,6-dimethyl-4-(tert-octyl)phenoxy, 2,6-diethyl-4-(tert-octyl)phenoxy, 2,6-diisopropyl-4-(tert-octyl)phenoxy, 2,6-di(2-butyl)-4-(tert-octyl)phenoxy, 2,6-di(n-butyl)-4-(tert-octyl)phenoxy, 2,6-di(2-hexyl)-4-(tert-octyl)phenoxy, 2,6-di(n-hexyl)-4-(tert-octyl)phenoxy, 2,6-di(2-dodecyl)-4-(tert-octyl)phenoxy, 2,6-di(n-dodecyl)-4-(tert-octyl)phenoxy and 2,6-dicyclohexyl-4-(tert-octyl)phenoxy;

2,6-dimethylthiophenoxy, 2,6-diethylthiophenoxy, 2,6-diisopropylthiophenoxy, 2,6-di(2-butyl)thiophenoxy, 2,6-di(n-butyl)thiophenoxy, 2,6-di(2-hexyl)thiophenoxy, 2,6-di(n- hexyl)thiophenoxy, 2,6-di(2-dodecyl)thiophenoxy, 2,6-di(n-dodecyl)thiophenoxy, 2,6-dicyclohexylthiophenoxy, 2,6-dimethyl-4-(n-butyl)thiophenoxy, 2,6-diethyl-4-(n-butyl)thiophenoxy, 2,6-diisopropyl-4-(n-butyl)thiophenoxy, 2,6-di(2-butyl)-4-(n-butyl)-thiophenoxy, 2,4,6-tri(n-butyl)thiophenoxy, 2,6-di(2-hexyl)-4-(n-butyl)thiophenoxy, 2,6-di(n-hexyl)-4-(n-butyl)thiophenoxy, 2,6-di(2-dodecyl)-4-(n-butyl)thiophenoxy, 2,6-di(n-dodecyl)-4-(n-butyl)thiophenoxy, 2,6-dicyclohexyl-4-(n-butyl)thiophenoxy, 2,6-di-methyl-4-(n-nonyl)thiophenoxy, 2,6-diethyl-4-(n-nonyl)thiophenoxy, 2,6-diisopropyl-4-(n-nonyl)thiophenoxy, 2,6-di(2-butyl)-4-(n-nonyl)thiophenoxy, 2,6-di(2-butyl)-4-(n-nonyl)thiophenoxy, 2,6-di(2-hexyl)-4-(n-nonyl)thiophenoxy, 2,6-di(n-hexyl)-4-(n-nonyl)-thiophenoxy, 2,6-di(2-dodecyl)-4-(n-nonyl)thiophenoxy, 2,6-di(n-dodecyl)-4-(n-nonyl)-thiophenoxy, 2,6-dicyclohexyl-4-(n-nonyl)thiophenoxy, 2,6-(dimethyl)-4-(n-octadecyl)-thiophenoxy, 2,6-(diethyl)-4-(n-octadecyl)thiophenoxy, 2,6-diisopropyl-4-(n-octadecyl)-thiophenoxy, 2,6-di(2-butyl)-4-(n-octadecyl)thiophenoxy, 2,6-di(2-butyl)-4-(n-octadecyl)thiophenoxy, 2,6-di(2-hexyl)-4-(n-octadecyl)thiophenoxy, 2,6-di(n-hexyl)-4-(n-octa-decyl)thiophenoxy, 2,6-di(2-dodecyl)-4-(n-octadecyl)thiophenoxy, 2,6-di(n-dodecyl)-4-(n-octadecyl)thiophenoxy, 2,6-dicyclohexyl-4-(n-octadecyl)thiophenoxy, 2,6-dimethyl-4-(tert-butyl)thiophenoxy, 2,6-diethyl-4-(tert-butyl)thiophenoxy, 2,6-diisopropyl-4-(tert-butyl)thiophenoxy, 2,6-di(2-butyl)-4-(tert-butyl)thiophenoxy, 2,6-di-(n-butyl)-4-(tert-butyl)thiophenoxy, 2,6-di(2-hexyl)-4-(tert-butyl)thiophenoxy, 2,6-di(n-hexyl)-4-(tert-butyl)thiophenoxy, 2,6-di(2-dodecyl)-4-(tert-butyl)thiophenoxy, 2,6-di(n-dodecyl)-4-(tert-butyl)thiophenoxy, 2,6-dicyclohexyl-4-(tert-butyl)thiophenoxy, 2,6-dimethyl-4-(tert-octyl)thiophenoxy, 2,6-diethyl-4-(tert-octyl)thiophenoxy, 2,6-diisopropyl-4-(tert-octyl)thiophenoxy, 2,6-di(2-butyl)-4-(tert-octyl)thiophenoxy, 2,6-di-(n-butyl)-4-(tert-octyl)thiophenoxy, 2,6-di(2-hexyl)-4-(tert-octyl)thiophenoxy, 2,6-di(n-hexyl)-4-(tert-octyl)thiophenoxy, 2,6-di(2-dodecyl)-4-(tert-octyl)thiophenoxy, 2,6-di(n-dodecyl)-4-(tert-octyl)thiophenoxy and 2,6-dicyclohexyl-4-(tert-octyl)thiophenoxy.

Specific examples of the R and $R^1$ to $R^{10}$ and D radicals occurring in the inventive formulae and their substituents include:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetraoxatetradecyl;

2-methylthioethyl, 2-ethylthioethyl, 2-propylthioethyl, 2-isopropylthioethyl, 2-butylthioethyl, 1- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butyl-phenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di-(o-tolyl)phosphino and diphenylphosphinoxido;

chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclo-pentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-secbutylcyclohexyl, 3- and 4-tert-butylcyclohexyl, cycloheptyl, 2-, 3- and 4-methyl-cycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methyliso-indolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydro-isoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-secbutylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The following formulae of specific rylene imide derivatives I sets forth particularly preferred examples of the rylene structures of the rylene imide derivatives with azide substituents. according to the invention

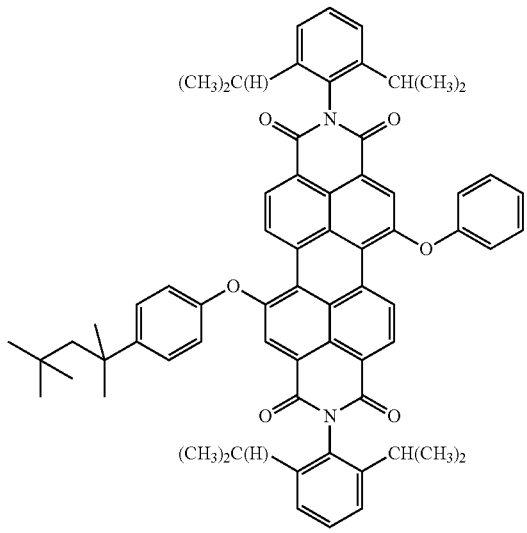

I1

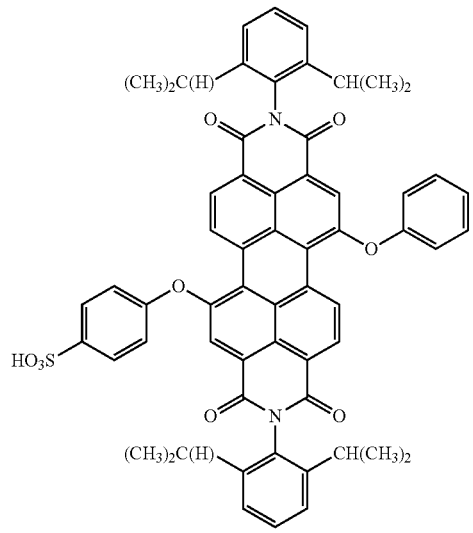

I2

I3
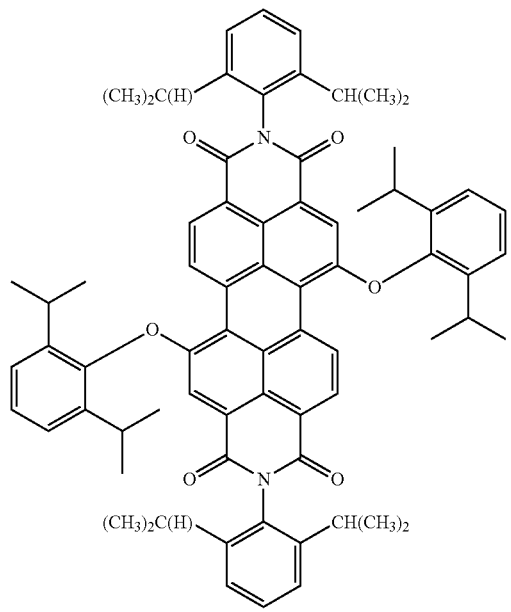
I4
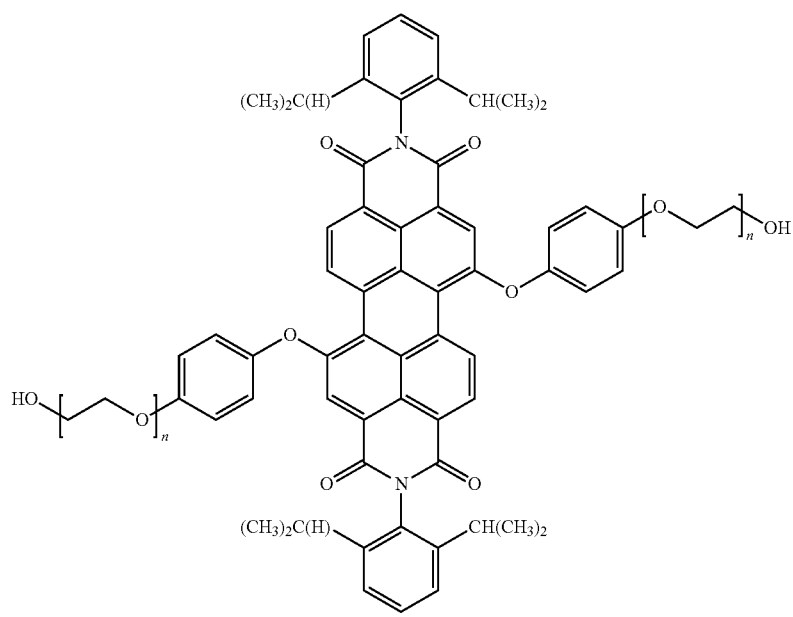

-continued
I5
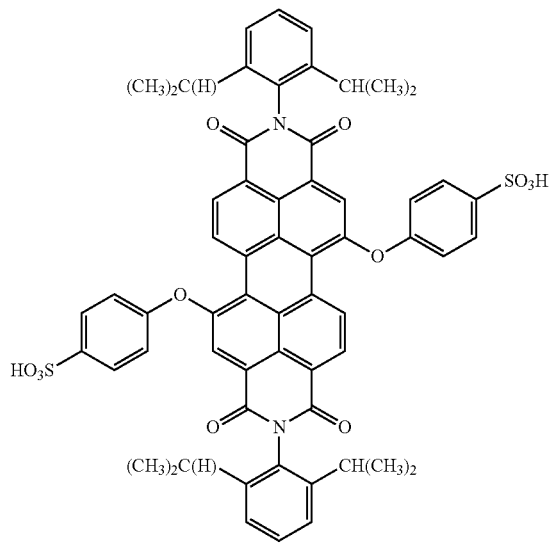
I6
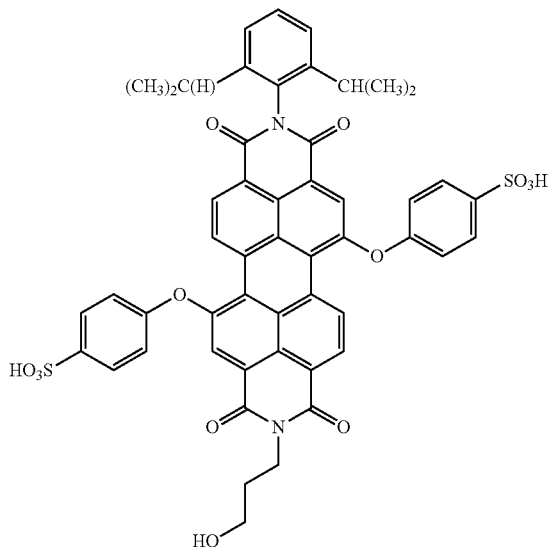
I7
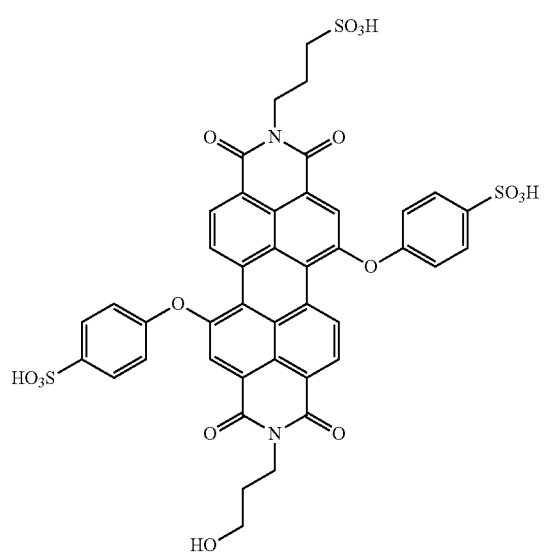
I8
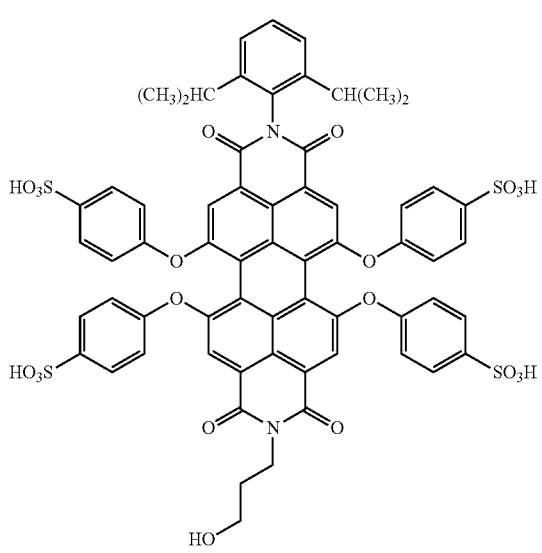

-continued

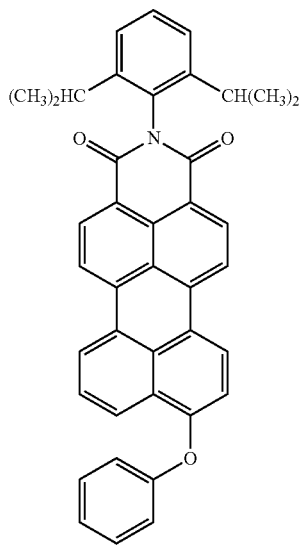

I9

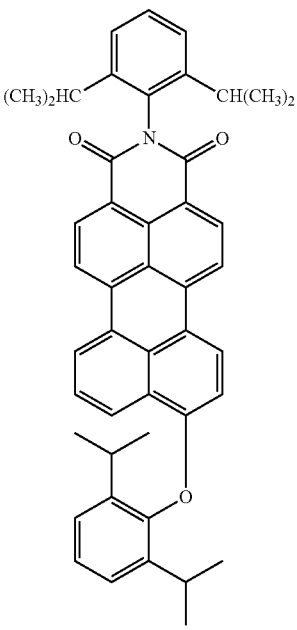

I10

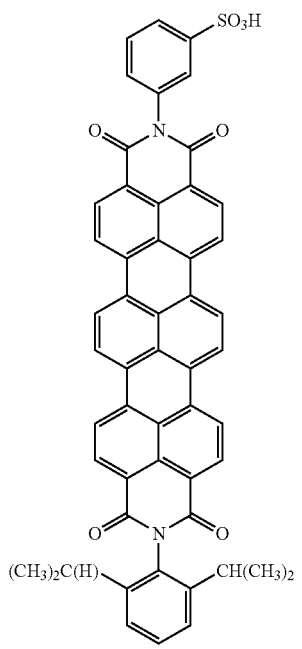

I11

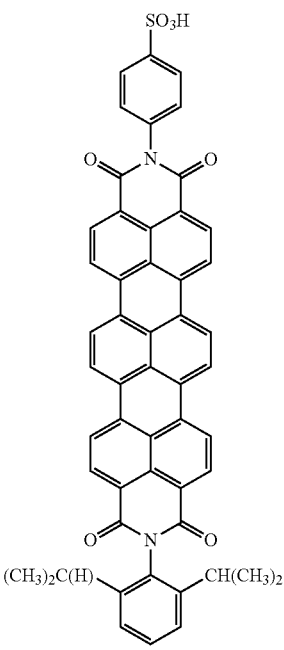

I12

Processes for the manufacture of the rylene imide derivatives without the azide group are known in the art and described in a number of patent applications describing such compounds. Reference is made to WO 2007/054470, WO 2007/006717, WO 2005/070895, DE 1 95 47 210, DE 103 08940 and DE 10308941. Processes for the manufacture of naphthalene diimides are disclosed in Chem. Soc. Rev. 2008, 37, 331-342, to which reference is made herewith.

As mentioned before, the azide groups can be introduced in accordance with known methods.

In one embodiment of the invention the compounds of formula I are present in form of their salts, preferably as sulfonate (—$SO_3^-$) salts. Especially as alkali-, earth alkali or quaternary ammonium sulfonate salts the compounds of the invention are water soluble and facilitate analysis, preferably of DNA, cells, biological tissues or biological fluids in aqueous medium.

Preferred sulfonate (—SO$_3^-$) salts are the following sodium salts of the compounds of the invention:

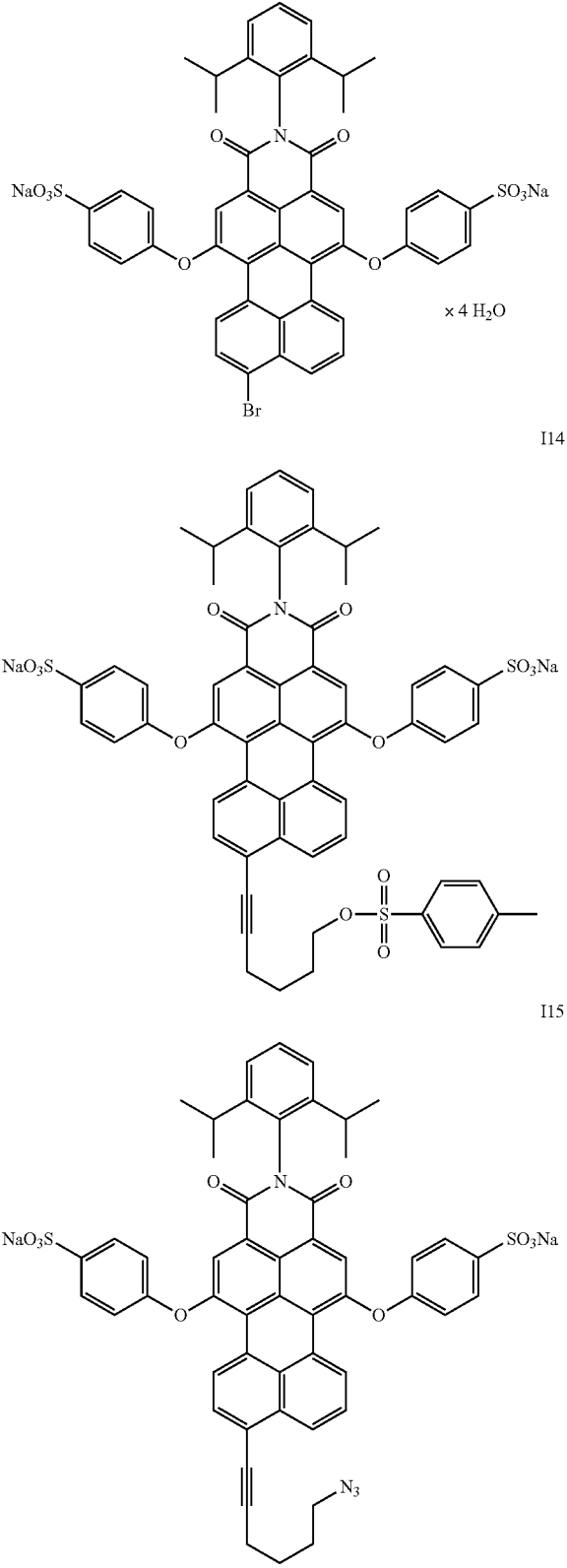

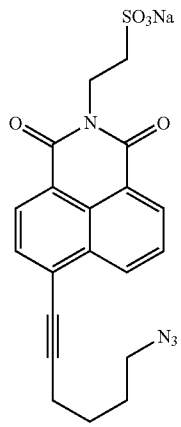

The novel mono azide substituted rylene imide derivatives according to the invention can be used as marker compounds for the detection of analytes. Due to their high absorption coefficients high-sensitivity analyses are possible which allow the detection of very small amounts of the analytes. For analytical purposes, the novel derivatives are preferably coupled via complex formation or via chemical bonding to substrates of target molecules and thereafter the detection is carried out by known spectroscopic methods, which are well known in the art.

The use of the novel rylene imide derivatives in so called Click-reactions is particularly preferred and constitutes a further embodiment of the present invention.

As mentioned before by Click-reaction a reaction of a terminal alkyne with an azide is designated which has been discovered more than 100 years ago. It has been particularly intensively studied by the group of Prof. Huisgen. However, due to the severe conditions necessary for carrying out the reaction and the risks associated under such reaction conditions with azides, the reaction has not found a wide use until in 2001, independently the groups of Prof. Meldal and of Prof. Sharpless discovered that the reaction can be effectively catalysed by various metals. This has been described in a number of patent applications of which WO 2003/101972 is mentioned here as an example.

Thus, a click chemistry ligation reaction between a first reactant having a terminal alkyne moiety and second reactant having an azide moiety for forming a product having a triazole moiety can be catalyzed by an addition of a catalytic amount of a metal salt having a metal ion selected from the group consisting of Cu, Au, Ag, Hg, Cd, Zr, Ru, Fe, Co, Pt, Pd, Ni, Rh, and W. In a preferred mode, the click chemistry ligation reaction is performed in the presence of a reducing agent for reducing said metal ion to a catalytically active form. Preferred reducing agents include ascorbate, quinone, hydroquinone, vitamin K, glutathione, cysteine, Fe$^{2+}$, Co$^{2+}$, an applied electric potential, and a metal selected from the group consisting of Al, Be, Co, Cr, Fe, Mg, Mn, Ni, and Zn.

According to a preferred variant, the reaction between a terminal alkyne and an azide for forming a product having a triazole moiety is performed in an aqueous solution and is catalyzed by a catalytic amount of copper (I). In a particularly preferred mode of this embodiment, the first and second reactants are present in equimolar amounts.

The click-reaction between a terminal alkyne and an azide can also be performed in a solvent containing a catalytic amount of a metal ion. The metal ions are preferably selected from the group of metals consisting of Cu, Au, Ag, Hg, Cd, Zr, Ru, Fe, Co, Pt, Pd, Ni, Rh, and W. The metal ion contributes directly or indirectly to a catalysis of the click chemistry ligation reaction. The metal ion is coordinated to a ligand for solubilizing such metal ion within the solvent, for inhibiting oxidation of such metal ion, and for dissociating, in whole or in part, from such metal ion during the catalysis of the click chemistry ligation reaction by said metal ion. A preferred ligand is acetonitrile. Another preferred ligand is a cyanide, nitrile, or isonitrile. Another preferred ligand is water. Other preferred ligands include primary, secondary, or tertiary amines, a nitrogen bearing heterocycle, carboxylate, halide, alcohol, thiol, sulfide, phosphine, and phosphite. Other preferred ligands are polyvalent and include one or more functional groups selected from the group consisting of nitrile, isonitrile, primary, secondary, or tertiary amine, a nitrogen bearing heterocycle, carboxylate, halide, alcohol, thiol, sulfide, phosphine, and phosphite.

The process using Cu (I) as a catalyst is experimentally simple and appears to have enormous scope. While a number of copper (I) sources can be used directly, it is also possible to prepare the catalyst by reduction of $Cu^{II}$ salts, which are less costly and often purer than $Cu^{I}$ salts ($CuSO_4$ $5H_2O$ serves well). As the reductant, ascorbic acid and/or sodium ascorbate proved to be excellent, for they allow preparation of the products in high yields and purity at 0.25-2 mol % catalyst loading.

The reaction appears to be very forgiving and does not require any special precautions. It proceeds normally to completion in 6 to 36 hours at ambient temperature in a variety of solvents, including aqueous t-butanol or ethanol and, very importantly, water with no organic co-solvent. Starting materials do not need to be dissolved in the reaction solvent. The reaction seems to proceed just as effectively as long as adequate stirring is maintained. Although most experiments were preformed at near neutral pH, the catalysis seems to proceed well at pH values ranging from ca. 4 to 12. The catalytic process is very robust and insensitive to usual reaction parameters.

It is further possible that $Cu^0$ can also be used as source of the catalytic species. Although these reactions may take longer to proceed to completion, the experimental procedure is also simple.

Copper (I) salts, for example CuI, $CuOTf \times C_6H_6$ and $[Cu(NCCH_3)_4]PF_6$, can also be used directly in the absence of a reducing agent. These reactions may require acetonitrile as co-solvent and one equivalent of a nitrogen base (e.g. 2,6-lutidine, triethylamine, diisopropylethylamine, or pyridine). In addition, formation of undesired byproducts, primarily diacetylenes, bis-triazoles, and 5-hydroxytriazoles, is sometimes observed.

Thus, although a broad range of both acetylene and azide components react readily in the acetonitrile systeme, the simple $Cu^{II}$/ascorbate aqueous system (with or without co-solvents and amine buffers/additives) is sometimes advantageous.

The Cu catalyzed reaction in addition is regiospecific as it yields 1,4-disubstituted 1,2,3-triazoles exclusively.

The monoazide substituted naphthylene or rylene-imide derivatives in accordance with the present invention are particularly suitable for use in click-reactions and respective reagent kits for detecting analytes in a sample, in particular biological samples.

Generally respective methods comprise the steps
(i) providing a sample;
(ii) contacting the sample with a functionalized compound comprising at least one functional group which is a first reaction partner for a click reaction under conditions wherein said compound forms an association product with the analyte to be detected,
(iii) contacting the association product with a second reaction partner for a click reaction under conditions wherein a click reaction between the first and second reaction partner occurs, wherein the second reaction partner is a monoazide substituted naphthylene or rylene-imide derivative in accordance with the present invention and
(iv) detecting the marker groups in the compounds in accordance with the present invention.

A further embodiment of this invention relates to a reagent kit for detecting an analyte in a sample, comprising:
(a) a functionalized compound comprising at least one functional group which is a first reaction partner for a click reaction,
(b) a second reaction partner for a click reaction, wherein the second reaction partner further comprises a marker group said second reaction partner being selected from the monoazide substituted naphthylene or rylene-imide derivatives in accordance with the present invention.

The use of the new naphthylene or rylene-imide derivatives according to this invention allows highly sensitive detection of an analyte, e.g. nucleic acids or nucleic acid binding proteins, in biological samples, e.g. clinical samples, environmental samples or agricultural samples. Preferred applications include, but are not limited to, the detection of genetic variabilities, e.g. single nucleotide polymorphisms (SNPs), pesticide or medicament resistance, tolerances or intolerances, genotyping, e.g. the detection of species or strains of organisms, the detection of genetically modified organisms or strains, or the detection of pathogens or pests, and the diagnosis of diseases, e.g. genetic diseases, allergic diseases, autoimmune diseases or infectious diseases. A further preferred application is the detection of nucleic acids in samples for brand protection, wherein products such as agricultural products, food products, or goods of value and/or packaging of these products are encoded with product-specific information, e.g. but not limited to, production site, date of production, distributor etc., and wherein this information is detected with the methods as described above.

The detection of the analyte may be a qualitative detection, e.g. the determination of the presence or absence of an analyte, e.g. a specific nucleic acid sequence in the sample to be analysed. The invention, however, also allows quantitative detection of an analyte, e.g. a nucleic acid sequence, in the sample to be analysed. Qualitative and/or quantitative detection may comprise the determination of labelling groups according to methods known in the art.

The analyte to be detected is preferably selected from nucleic acids and nucleoside-, nucleotide- or nucleic acid-binding molecules, e.g. nucleoside-, nucleotide- or nucleic acid-binding proteins. More preferably, the analyte is a nucleic acid, e.g. any type of nucleic acid which can be detected according to known techniques, particularly hybridization techniques. For example, nucleic acid analytes may be selected from DNA, e.g. double-stranded or single-stranded DNA, RNA, or DNA-RNA hybrids. Particular examples of nucleic acid analytes are genomic DNA, mRNA or products derived therefrom, e.g. cDNA.

The detection can be carried out according to any known test format which is suitable for the detection of analytes, particularly nucleic acid analytes in a sample. For example, the method may involve the detection of analytes immobilized on solid surfaces such as membranes, e.g. in Southern or Northern blots, chips, arrays or particles such as beads. Further, the detection can be carried out in gels, e.g. after electrophoretic separation of the sample in gels, e.g. agarose or polyacrylamide gels. The method may involve the detection of single analytes or the parallel detection of a plurality of analytes, e.g. in a chip or microarray format.

The sample may be any sample which may contain the analyte to be detected. For example, the sample may be a biological sample, such as an agricultural sample, e.g. a sample comprising plant material and/or material associated with the site where plants grow, plant materials are stored or processed. On the other hand, the sample may also be a clinical sample, such as a tissue sample or a body fluid sample such as blood, serum, plasma, etc., particularly of human origin. Further types of samples include, but are not limited to, environmental samples, soil samples, food samples, forensic samples or samples from valuable goods which are tested for brand protection.

Due to this high sensitivity, the detection using the new compounds according to the instant invention is suitable for detecting analytes directly without amplification. According to the invention, even minute amounts of analytes, e.g. of nucleic acids, e.g. 0.1 ng or lower, preferably 0.01 ng or lower, more preferably 1 pg or lower, still more preferably 0.1 pg or lower, even more preferably 0.01 pg or lower and most preferably 0.001 pg or lower may be determined even without amplification. An especially high sensitivity may be obtained by incorporating multiple modified nucleotides into a nucleic acid molecule by using unprotected aldehyde groups and/or by using optimized staining techniques. For example, the detection of an analyte, e.g. a gene, in a biological sample, might be performed by a combination of Southern blotting and the instant method. It should be noted, however, that the method also allows the detection of nucleic acids combined with an amplification step, which may be carried out according to known protocols such as PCR or modifications thereof, such as asymmetric PCR, real-time PCR, reverse transcription PCR, etc., or other amplification protocols such as LCR.

Preferably, a sequence-specific detection of the analyte can be carried out, wherein for example a nucleic acid having a specific sequence is distinguished from other nucleic acid sequences in the sample of a polypeptide capable of binding a specific nucleic acid sequence is distinguished from other polypeptides in the sample. Such a sequence-specific detection preferably comprises a sequence-specific hybridization reaction by which the nucleic acid sequence to be detected is associated with the novel compound according to the present invention. It should be noted, however, that the sequence-unspecific detection of nucleic acids, e.g. detection of any nucleic acids present in a sample is also possible.

The functionalized compound may comprise a single functional group or a plurality of functional groups. For example, a functionalized compound may be coupled to a dendrimeric moiety comprising a plurality, e.g. 2, 3, 4, 5, 6, 7, 8 or more functional groups as indicated above. Dendrimeric moieties may be synthesized by known techniques.

The functional group of the functionalized compound is attached to a compound which is capable of forming an association product with the analyte. The compound may be a nucleosidic or nucleotidic compound, e.g. a nucleoside or nucleoside analogue or a nucleotide or nucleotide analogue or an oligomer or polymer comprising at least one functionalized compound, e.g. a nucleic acid or nucleic acid analogue. A nucleosidic or nucleotidic compound is a nucleoside or nucleotide analogue or a nucleotide or nucleotide analogue capable of being incorporated into nucleic acids or nucleic acid analogues, e.g. by chemical or enzymatic methods. The resulting nucleic acid or nucleic acid analogue should be capable of forming association products, e.g. nucleic acid hybrids, with the analyte. Preferably, the compound comprises a base moiety, e.g. a nucleobase or another heterocyclic base moiety capable of forming base pairs with a nucelobase, and a backbone moiety, e.g. comprising a sugar moiety and optionally a phosphate moiety in nucleosides or nucleotides or a different backbone moiety in nucleoside or nucleotide analogues.

Preferred examples of functional nucleosidic compounds, are those wherein the nucleobase is 7-dN-G, C, 7-dN-A or T.

Preferably, the functional group is attached to a base moiety, e.g. to a nucleobase. The functional group, however, may also be attached to a backbone moiety, e.g. a sugar group, a phosphate group, or in the case of nucleoside or nucleotide analogues, a modified sugar group, a modified phosphate group or peptide backbone moiety, etc. Preferably, the functional group is covalently attached to the compound via a direct bond or via a spacer. If the attachment is effected via a spacer, the functional group may be linked to an aliphatic or cycloaliphatic group, an aromatic or heteraromatic group, an alkene group and/or an alkyne group. More preferably, the functional group may be linked to aromatic heteroaromatic groups or to alkyne groups. Especially preferred aldehyde groups include aromatic and aliphatic aldehyde groups such as benz-aldehyde, or aldehyde groups in aldoses such as trioses, tetroses, pentoses or hexoses like glucose or mannose.

The functional group of the functionalized compound is preferably a terminal alkyne group, which, by reaction with a novel compound in accordance with this invention, yields a metal, preferably copper catalyzed, (3+2) cycloaddition between an azide and an alkyne group. The irreversible formation of 1,2,3-triazoles as a result of the azide/alkyne cycloaddition is orthogonal, the required chemical groups are small (incorporation with minimal disruption of the biomolecule's environment) and selective due to the lack of azides and alkynes found in nature.

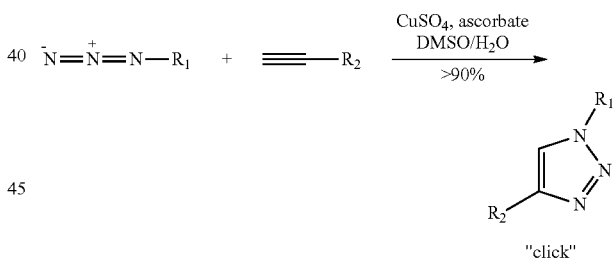

wherein $R_1$ and $R_2$ are organic radicals.

The click-functionalized group is preferably attached to a nucleobase which may be selected from naturally occurring and non-naturally occurring purine and pyrimidine bases. Preferably, the nucleobases are selected from cytidine, uracil, thymine, adenine, guanine, 7-deazaadenine, 7-deazaguanine, inosine and xanthine. The functional group is preferably attached to position 5 or 6, more preferably to position 5, of a pyrimidine nucleobase or to position 7 or 8, more preferably to position 7 of a purine nucleobase, particularly if an enzymatic incorporation into a nucleic acid is desired.

The functional group may be covalently attached to the compound, e.g. via a direct bond or a spacer, e.g. a spacer having a chain length up to 20 atoms. The spacer may be a flexible spacer, e.g. an alkylene-based spacer, optionally containing heteroatoms such as O, S and/or N or an at least partially rigid spacer, e.g. a spacer which comprises at least one rigid group selected from alkene groups, alkyne groups, cyclic groups, particularly aromatic or heteroaromatic groups, but also cycloaliphatic groups and combinations thereof.

The functionalized compound should be capable of forming an association product with the analyte to be detected. On the one hand, the functionalized compound may be selected from compounds which can be incorporated into nucleic acids or nucleic acid analogues, i.e. nucleic acid or nucleic acid analogues building blocks. Preferred examples of such compounds are Click-functionalized nucleotides or nucleotide analogues. On the other hand, the functionalized compound may be selected from nucleic acids or nucleic acid analogues or Click-functionalized nucleic acids or analogues.

The term "nucleotide" according to the present invention particularly relates to ribonucleotides, 2'-deoxyribonucleotides or 2',3'-dideoxyribonucleotides. Nucleotide analogues may be selected from sugar- or backbone modified nucleotides, particularly of nucleotide analogs which can be enzymatically incorporated into nucleic acids. In preferred sugar-modified nucleotides the 2'-OH or H-group of the ribose sugar is replaced by a group selected from OR, R, halo, SH, SR, $NH_2$, NHR, $NR_2$ or CN, wherein R is $C_1$-$C_6$ alkyl, alkenyl or alkynyl and halo is F, Cl, Br or I. The ribose itself can be replaced by other carbocyclic or heterocyclic 5- or 6-membered groups such as a cyclopentane or a cyclohexene group. In preferred backbone modified nucleotides the phospho(tri) ester group may be replaced by a modified group, e.g. by a phosphorothiate group or a H-phosphonate group. Further preferred nucleotide analogues include building blocks for the synthesis of nucleic acid analogs such as morpholino nucleic acids, peptide nucleic acids or locked nucleic acids.

Click-functionalized nucleic acids may be oligonucleotides, e.g. nucleic acids having a length of up to 30 nucleotide (or nucleotide analogue) building blocks or polynucleotides having a length of more than 30 nucleotide (or nucleotide analogue) building blocks. Preferably, the nucleic acids and nucleic analogues are capable of specific binding to the analyte, e.g. capable of hybridizing with a nucleic acid analyte under assay conditions. The minimum length is preferably 12 and more preferably 14 nucleotide (or nucleotide analogue) building blocks.

Functionalized nucleic acid or nucleic acid analogue building blocks may be incorporated into nucleic acids by standard techniques for chemical synthesis and/or by enzymatic incorporation. Chemical synthesis for example may be carried out by standard phosphoramidite chemistry using modified nucleoside phosphoramidites as building blocks in standard synthesis protocols. Other types of preferred building blocks for chemical synthesis include H-phosphonate or phosphorotriester modified nucleosides.

On the other hand, modified nucleotides may be incorporated into nucleic acids by enzymatic methods. Surprisingly, it was found that aldehyde- or Click-functionalized nucleoside triphosphates are accepted as enzyme substrates by nucleic acid synthesizing enzymes such as DNA polymerases, RNA polymerases, reverse transcriptases or telomerases. For example, it was found that modified nucleoside triphosphates are accepted by DNA polymerases commonly used for primer extension and amplification protocols, e.g. thermostable DNA polymerases such as Taq polymerase, Vent polymerase, Pfx polymerase, Pwo polymerase, or Therminator polymerase as described in example 7. Enzymes accept modified triphosphates without loss in fidelity and allow a template-based incorporation into nucleic acids such as DNA an RNA.

There are several possibilities for the analyte detection. For example, functionalized nucleic acid building blocks, e.g. nucleotides or nucleotide analogues, together with appropriate enzymes, may be provided which are enzymatically incorporated into a nucleic acid molecule which forms the association product with the analyte. In the present invention, a single type of functionalized nucleotide or a plurality of different types of functionalized nucleotides may be employed. Alternatively or additionally, a functionalized nucleic acid or nucleic acid analogue may already be present, which has been manufactured, e.g. by chemical or enzymatic synthesis, and which specifically binds, e.g. by hybridization to the analyte to be detected.

In a preferred embodiment the method comprises a primer extension reaction optionally in combination with subsequent nucleic acid amplification steps such as PCR. For example, at least one primer molecule may be provided which hybridizes under assay conditions with a nucleic acid analyte to be detected or the complement thereof. The bound primer is then extended wherein a detectable extension product is obtained which is indicative for the presence and/or amount of the nucleic acid analyte to be detected. According to this embodiment, functionalized primers and/or functionalized nucleotides or nucleotide analogues for incorporation into the extension product may be used.

Alternatively and/or additionally the method may comprise the use of functionalized hybridization probes which hybridize under the assay conditions with the nucleic acid analyte to be detected or the complement thereof wherein the formation of a hybridization product is indicative for the presence and/or amount of the nucleic acid analyte to be detected.

The detection method may be carried out by any known nucleic acid detection protocols, e.g. involving the use of solid supports. For example, a solid support, e.g. a chip or array or a particulate material such as a bead may be provided to which a capture probe is bound capable of hybridizing to the analyte to be detected. The solid phase bound nucleic acid analyte may be detected by using functionalized hybridization probes which hybridize with the nucleic acid analyte in a different sequence part as the capture probe does and subsequent detection of the bound hybridization probe, e.g. with a metallization reagent. This method is particularly suitable for the diagnostic applications in the agricultural and clinical field, e.g. for the detection of DNA and/or mRNA from plants, e.g. genetically modified plants, DNA from pathogens or plant pests etc.

An important aspect is the detection of genetic variabilities, e.g. single nucleotide polymorphisms (SNPs). The genome of, for example humans, contains nucleotide sequence variations at an average frequency of up to 0.1%. Therefore, these variabilities provide excellent markers for the identification of genetic factors contributing to complex disease susceptibility.

For example, the detection of nucleic acid matches or mismatches, e.g. in SNPs, may comprise the use of functionalized hybridization probes which hybridize under the assay conditions with the nucleic acid analyte to be detected for the complement thereof and subjecting the hybridization product to a treatment procedure wherein a hybridization product containing at least one mismatch is dissolved and wherein the presence of an undissolved hybridization product is indicative for the presence and/or amount of a nucleic acid which has a fully complementary sequence (i.e. no mismatch) to the hybridization probe.

The treatment for the dissolution of mismatch-containing hybridization products may comprise a mismatch digestion treatment, i.e. the use of mismatch detecting enzymes which cleave the hybridization product depending on the presence of a mismatch. Suitable enzymes for such a mismatch digestion treatment include mismatch-glycosylase such as those encoded by the genes hMSH2 and hMLH1 and Mut, S, Mut L and Mut H. Additional proteins are MutY and Mig.Mth1. Mig.Mth1 cuts T out of a TG mismatch, MutY cuts out A in an AG mismatch and the enzyme TDG cuts out T in a TG mismatch.

Alternatively or additionally, mismatch-containing hybridization products may be dissolved by a differential hybridization treatment involving the adjustment of hybridization conditions, e.g. in view of temperature, salt concentration and/or washing with dimethyl ammonium chloride, wherein a mismatch containing hybridization product is dissolved and the fully complementary hybridization product remains stable.

In a still further variant mismatch, e.g. SNPs, may be determined by enzyme-catalyzed selective primer elongation. For this purpose a primer is provided, wherein the 3' end of the primer is directly located upstream of a potential mismatch site on the template analyte. A primer extension is only possible when a nucleotide which is complementary to the next base on the template is present. By selecting a single type of functionalized nucleotide and determining whether it is incorporated into the primer or not, the base on the potential mismatch site can be determined.

Preferably the reagent kits comprising the novel monoazide substituted rylene-imide derivatives of the present invention are used for agricultural applications. For example for the detection of nucleic acids from plants, plant pathogens or plant pests such as viruses, bacteria, fungi or insects, for detecting genetic variabilities, e.g. SNPs in plants or plant parts, plant pathogens or plant pests such as insects.

A further application is a detection or monitoring of herbicide, fungicide or pesticide resistances, tolerances or intolerances, e.g. resistances, tolerances or intolerances in fungi, insects or plants in organisms or populations of organisms. The detection method is also suitable for rapid genotyping, e.g. for the rapid detection and/or differentiation of species or strains of fungi, insects, or plants. Further, detection and/or differentiation of genetically modified organisms for strains, e.g. organisms or strains of fungi, insects or plants is possible.

Due to high sensitivity early diagnostic of pathogens is possible, i.e. diagnostics before first symptoms of the presence of pathogens is visible. This is particularly important for the diagnosis of soy rust (*Phakospora pachyrizi*) or other pathogens, e.g. *Blumeria graminis, Septoria tritici* or Oomycetes or other pathogens for which control is only possible, if their presence is detected before is can be visually recognized.

Further, the detection method is suitable for medical, diagnostic and forensic applications, e.g. in human or veterinary medicine, e.g. for the detection of nucleic acids from pathogens, e.g. human pathogens or pathogens of livestock or pet animals.

Further preferred applications include the detection of genetic variabilities, e.g. SNPs in humans or the detection of medicament resistances, tolerances or intolerances or allergies, for genotyping, particularly genotyping of humans in order to determine mutations associated with predisposition or enhanced risk of disorders, allergies and intolerances and for the detection of genetically modified organisms or strains, organisms or strains of bacteria or viruses but also genetically modified life stock animals etc., for the rapid diagnosis of diseases, e.g. genetic diseases, allergic diseases, autoimmune diseases or infectious diseases and for detecting the function and/or expression of genes, e.g. research purposes.

Further applications can be found in WO 2005/117 161.

EXAMPLE 1 a) Synthesis of N-(2,6-diisopropylphenyl)-9-(6-hydroxy-1-hexinyl)-perylene-2,4-dicarboxylic acid imide A degassed mixture of 25 mg (0.27 mmoles) 6-hexinol, 123 mg (0.94 mmoles) Huenig-base and 1 ml dimethylformamide (DMF) was added within 15 min. to a degassed solution of 160 mg (0.286 mmoles) N-(2,6-diisopropylphenyl)-9-bromo-perylene-3,4-dicarboxylic acid amide (prepared in accordance with WO 2001/016109) and 21 mg (0.114 mmoles) of Cu(I) iodide in 2 ml of DMF. After the further addition of 33 mg (0.029 mmoles) of tetrakis(triphenylphosphino)-palladium (0) the reaction mixture was stirred for 4 hours at room temperature, the solvent partially evaporated and purified on silica gel (solvent: methylene chloride:methanol, weight ratio 50:1). 60 mg (37% of the theoretical yield) of a red solid were obtained.

The NMR spectra correspond to the desired product:

$^1$H-NMR (CDCl$_3$, 400 MHz): δ [ppm]=8.79 (d, 1H, J=8 Hz), 8.74 (d, 1H, J=8 Hz), 8.67 (d, 1H, J=8 Hz), 8.57 (dd, 1H, $J_1$=8 Hz, $J_2$=4 Hz), 8.38 (d, 1H, J=8 hz), 7.83 (dd, 1H, $J_1$=16 Hz, $J_2$=8 Hz), 7.65-7.54 (m, 4H), 7.47 (dd, 1H, $J_1$=8 Hz, $J_2$=8 Hz), 7.35 (d, 1H, J=8 Hz), 4.48 (t, 2H, J=4 Hz), 4.08 (dd, 2H, $J_1$=8 Hz, $J_2$=4 Hz), 3.52 (dd, 1H, $J_1$=8 Hz, $J_2$=4 Hz), 3.17 (d, 1H, J=4 Hz), 2.70-2.66 (m, 1H), 1.74-1.68 (m, 2H), 1.05 (d, 12H, J=8 Hz).

b) Synthesis of N-(2,6-diisopropylphenyl)-9-(6-azido-1-hexinyl)-perylene-2,4-dicarboxylic acid imide 0.0135 ml (0.174 mmoles) of methane sulfonic acid chloride was added under nitrogen atmosphere to a solution of 13.5 mg (0.087 mmoles) of N-(2,6-diisopropylphenyl)-9-(6-hydroxy-1-hexinyl)-perylene-2,4-dicarboxylic acid imide and 0.036 ml (0.261 mmoles) triethyl amine in 6 ml of methylene chloride at a temperature of 0° C. After warming to room temperature, stirring was continued for 90 minutes. After addition of saturated sodium chloride solution the reaction mixture was diluted with 25 ml methylene chloride. The organic phase was separated and washed three times, two times with 25 ml saturated sodium chloride solution and once with 25 ml of water, dried over magnesium sulfate and then dried under reduced pressure. 51 mg of a dark red oil were obtained, which was dissolved in 6 ml DMF and thereafter 34 mg (0,522 mmoles) of sodium azide was added under nitrogen atmosphere). The reaction mixture was stirred at room temperature over night and thereafter diluted with 25 ml acetic acid ethyl ester. The organic phase was washed four times with saturated sodium chloride solution and twice with water, dried over magnesium sulfate and dried under reduced pressure. After chromatography with methylene chloride 16.5 mg of a dark red solid was obtained, the NMR spectrum of which corresponded to the desired product.

$^1$H-NMR (CDCl$_3$, 600 MHz): δ [ppm]=8.66-8.61 (m, 2H), 8.52-8.42 (m, 3H), 8.39 (dd, 1H, $J_1$=12 Hz, $J_2$=6 Hz), 8.34 (d, 1H, J=12 Hz), 7.73-7.67 (m, 2H), 7.47-7.44 (m, 1H), 7.32 (dd, 2H, $J_1$=12 Hz, $J_2$=6 Hz), 3.44-3.39 (m, 2H), 2.97-2.90 (m, 2H), 2.76-2.72 (m, 2H), 2.67 (dd, 1H, $J_1$=12 Hz, $J_2$=12 Hz), 1.92-1.81 (m, 2H), 1.17-1.15 (m, 12H).

EXAMPLE 2

Synthesis of N-(2,6-diisopropylphenyl)-9-(6-azido-1-hexinyl)-perylene-3,4-dicarboxylic acid imide a) N-(2,6-diisopropylphenyl)-9-(6-tosyloxy-1-hexinyl)-perylene-3,4-dicarboxylic acid imide

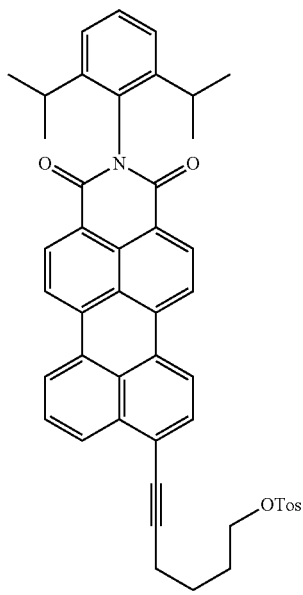

To a degassed mixture of 2.40 g (4.32 mmoles) of N-(2,6-diisopropylphenyl)-9-bromo-perylene-3,4-dicarboxylic acid imide (synthesized according to WO2001016109) and 0.576 g (3.36 mmoles) of Cu(I) iodide in 72 ml dimethylformamide (DMF) and 144 ml methylene chloride were added 2.00 g (1.72 mmoles) of tetrakis(triphenylphosphino)-palladium (0), 2.09 g (2.88 ml, 2.05 mmol) triethylamine and a degassed solution of 1.82 g (7.20 mmol) p-toluensulfonic acid-5-hexinyl ester (synthesized according to (Y. Yang and T. M. Swager, Macromolecules 2006, 39, 2013-2015) in 12 ml methylene chloride. The reaction mixture was stirred for 90 minutes at room temperature, subsequently the solvent was evaporated until dryness and purified on silica gel (solvent: toluene: methylene chloride: 10:1 to 1:1). 2.04 g (65% of the theoretical yield) of a red solid were obtained.

1H-NMR (CDCl3, 360 MHz): δ [ppm]=8.57 (mc, 2H), 8.18-8.28 (m, 4H), 8.10 (mc, 1H), 7.82 (mc, 2H), 7.47-7.57 (m, 3H), 7.32-7.38 (m, 4H), 4.18 (t, 2H), 2.82 (mc, 2H), 2.63 (t, 2H), 2.42 (s, 3H), 1.97 (mc, 2H), 1.82 (mc, 2H), 1.22 (d, 12H).

b) N-(2,6-diisopropylphenyl)-9-(6-azido-1-hexinyl)-perylene-3,4-dicarboxylic acid imide

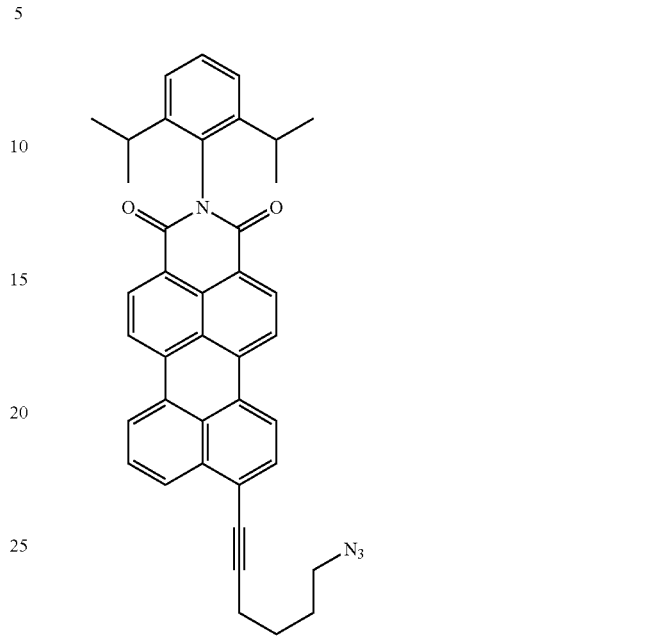

A solution of 1.00 g (1.36 mmol) N-(2,6-diisopropylphenyl)-9-(6-tosyloxy-1-hexinyl)-perylene-3,4-dicarboxylic acid imide and 0.60 g (9.1 mmol) sodium azide in 144 ml DMF were stirred for 20 hours at room temperature under nitrogen atmosphere.

The reaction mixture was extracted with 250 ml acetic acid ethyl ester and washed three times with water and one time with saturated sodium chloride solution. The organic phase was dried over magnesium sulphate and dried under reduced pressure.

The dried product was purified on silica gel (60 Å, 60-200 µm) with methylene chloride: n-heptane (4:1). After removing the solvent 0.6 g of a dark-red solid material were obtained which was solved in 23 ml chlorobenzene and 23 ml petroleum ether are layed above to protect the solution from the environment. After keeping 12 days in refrigerator, the solid material was aspirated and washed with petroleum ether and dried at 30° C. in the vacuum drying oven. 0.375 g (46% of the theoretical yield) of a dark red micro-crystal were obtained.

C40H34N4O2 Ber. C, 79.71; H, 5.69; N, 9.30; O, 5.31. (602.74) Gef. C, 79.5; H, 5.8; N, 9.2; O, 5.5

1H-NMR (CDCl3, 500 MHz): δ [ppm]=8.57-8.61 (m, 2H), 8.28-8.32 (m, 3H), 8.24 (mc, 1H), 8.17 (mc, 1H), 7.61 (mc, 1H), 7.57 (mc, 1H), 7.49 (mc, 1H), 7.35 (mc, 2H), 3.43 (t, 2H), 2.80 (mc, 2H), 2.69 (mc, 2H), 1.82-1.94 (m, 4H), 1.18 (d, 12H).

UV/Vis (CH2Cl2): λ max (e)=524 (42310), 500 (41230), 356 (3500), 344 nm (3700).

EXAMPLE 3

Synthesis of N-(2,6-diisopropylphenyl)-1,6-di-(4-suphonato-phenyloxy)-9-(6-azido-1-hexinyl)-perylene-3,4-dicarboxylic acid imide, di-sodium salt a) N-(2,6-diisopropylphenyl)-9-brom-perylene-3,4-dicarboxylic acid imide tetrahydrate, disodium salt

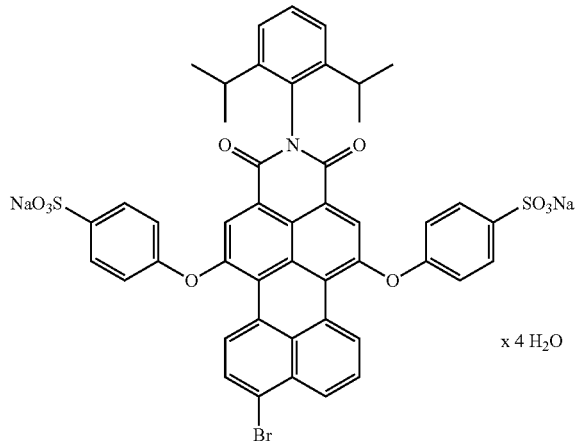

0.80 g (1.07 mmol) N-(2,6-diisopropylphenyl)-9-brom-perylene-3,4-dicarboxylic acid imide (synthesized according to WO96/22332) were stirred in 2.5 ml concentrated sulfuric acid for 4 hours at room temperature. After adding 20 ml of water with cooling the precipitation was separated by filtration. The solid material was taken up in water and the solution was neutralized with NaOH. After drying at 80° C. in a vacuum drying oven the residue was solved in methanol whereby the insoluble residue was separated by filtration. The filtrate was dried at 60° C. in the vacuum drying oven. 1.00 g (98% of the theoretical yield) of a red solid material were obtained. According to 1H-NMR-analysis the product contained 4 molecules water of crystallization per molecule.

1H-NMR (D6-DMSO, 400 MHz): δ [ppm]=9.27 (mc, 1H), 9.06 (mc, 1H), 8.29 (mc, 1H), 8.10 (mc, 3H), 7.86 (mc, 1H), 7.67 (mc, 4H), 7.44 (mc, 1H), 7.33 (mc, 2H), 7.19 (mc, 4H), 2.66 (hept., 2H), 1.05 (d, 12H).

b) N-(2,6-diisopropylphenyl)-1,6-di-(4-suphonato-phenyloxy)-9-(6-tosyloxy-1-hexinyl)-perylene-3,4-dicarboxylic acid imide, di-sodium salt

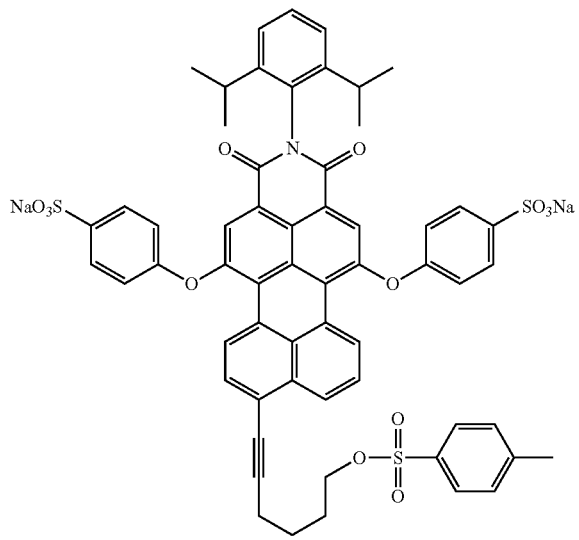

To a solution of 0.073 g (0.38 mmoles) of Cu(I) iodide in 30 ml of anhydrous DMF, degassed with argon, were added 0.23 g (0.20 mmol) of tetrakis(triphenylphosphino)-palladium (0) and 0.24 g (0.33 mmol) triethyl amin. After adding 0.21 g (0.82 mmol) p-toluensulfonic acid-5-hexinyl ester (synthesized according to (Y. Yang and T. M. Swager, Macromolecules 2006, 39, 2013-2015) in 2 ml DMF the reaction mixture was stirred for 3 hours at room temperature. The solvent was removed under vacuum at room temperature. The product (1.47 g) was purified on silica gel (solvent: methylene chloride:methanol; 4:1 and afterwards toluene:methanol; 2:1). 0.24 g (44% of the theoretical yield) of a dark red solid were obtained.

1H-NMR (D6-DMSO, 400 MHz): δ [ppm]=9.25 (mc, 1H), 9.14 (mc, 1H), 8.36 (mc, 1H), 8.09 (mc, 2H), 7.78 (mc, 3H), 7.68 (mc, 4H), 7.43 (mc, 4H), 7.31 (mc, 2H), 7.19 (mc, 4H), 4.12 (t, 2H), 2.75 (hept., 2H), 2.60 (t, 2H), 2.35 (s, 3H), 1.80 (mc, 2H), 1.63 (mc, 2H), 1.05 (d, 12H).

c) N-(2,6-diisopropylphenyl)-1,6-di-(4-suphonato-phenyloxy)-9-(6-azido-1-hexinyl)-perylene-3,4-dicarboxylic acid imide, di-sodium salt

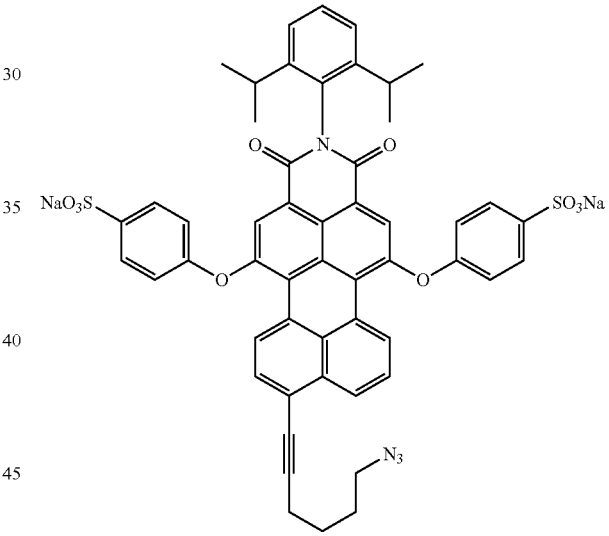

A solution of 0.24 g (0.21 mmol) N-(2,6-diisopropylphenyl)-1,6-di-(4-suphonato-phenyloxy)-9-(6-tosyloxy-1-hexinyl)-perylene-3,4-dicarboxylic acid imide, di-sodium salt and 0.096 g (1.47 mmol) sodium azide were stirred for 26 hours at room temperature.

The reaction mixture was filtrated. The filtrate was purified on silica gel (60 Å, 60-200 μm). The solvent was evaporated until dryness and remnants of solvent were removed under vacuum. The product (0.34 g) was purified on silica gel ((60 Å, 60-200 μm) solvent: methylene chloride:methanol; 4:1 to 2:1). 0.10 g (48% of the theoretical yield) of the product were obtained.

1H-NMR (D6-DMSO, 400 MHz): δ [ppm]=9.28 (mc, 1H), 9.18 (mc, 1H), 8.42 (mc, 1H), 8.07 (mc, 2H), 7.82 (mc, 2H), 7.66 (mc, 4H), 7.47 (mc, 1H), 7.30 (mc, 2H), 7.18 (mc, 4H), 3.44 (t, 2H), 2.58-2.73 (m., 4H), 1.75 (mc, 4H), 1.03 (d, 12H).

EXAMPLE 4

Synthesis of N-(2,6-diisopropylphenyl)-4-(6-azido-1-hexinyl)-naphthaline-1,8-dicarboxylic acid imide a) N-(2,6-diisopropylphenyl)-4-(6-tosyloxy-1-hexinyl)-naphthaline-1,8-dicarboxylic acid imide

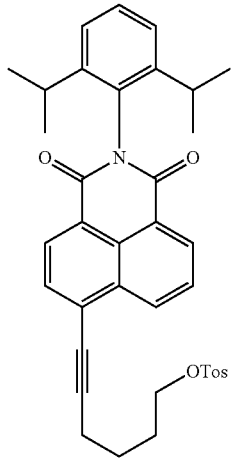

To a degassed mixture of 0.50 g (1.15 mmoles) of N-(2,6-diisopropylphenyl)-4-bromo-naphthaline-1,8-dicarboxylic acid imide (synthesized according to WO2007062002) and 0.17 g (0.89 mmoles) of Cu(I) iodide in 20 ml anhydrous dimethylformamide (DMF) and 40 ml anhydrous methylene chloride were added 0.53 g (0.46 mmoles) of tetrakis(triphenylphosphino)-palladium (0), 0.58 g (0.80 ml, 5.5 mmol) triethylamine and a degassed solution of 0.48 g (1.90 mmol) p-toluensulfonic acid-5-hexinyl ester (synthesized according to (Y. Yang and T. M. Swager, Macromolecules 2006, 39, 2013-2015) in 2 ml methylene chloride. The reaction mixture was stirred for 60 minutes at room temperature, subsequently the solvent was evaporated until dryness and purified on silica gel ((60 Å, 60-200 µm), first with methylene chloride and afterwards with n-heptane/acetic acid (3:1) as free-flow agent. 0.6 g (86% of the theoretical yield) of a orange-yellow oil were obtained.

1H-NMR (CDCl$_3$, 400 MHz): δ [ppm]=8.67 (mc, 2H), 8.56 (mc, 1H), 7.80-7.88 (m, 4H), 7.48 (mc, 1H), 7.33 (mc, 4H), 4.16 (t, 2H), 2.72 (mc, 2H), 2.64 (t, 2H), 2.45 (s, 3H), 1.94 (mc, 2H), 1.83 (mc, 2H), 1.14 (d, 12H).

b) N-(2,6-diisopropylphenyl)-4-(6-azido-1-hexinyl)-naphthaline-1,8-dicarboxylic acid imide

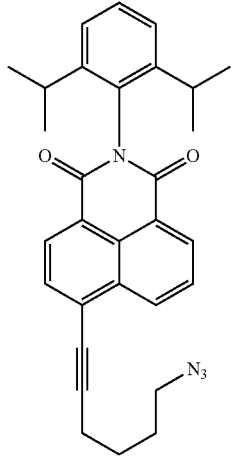 [SMILES: CC(C)c1cccc(C(C)C)c1N1C(=O)c2cccc3c(C#CCCCCN=[N+]=[N-])ccc(c23)C1=O]

A solution of 0.50 g (0.82 mmol) N-(2,6-diisopropylphenyl)-4-(6-tosyloxy-1-hexinyl)-naphthaline-1,8-dicarboxylic acid imide and 0.36 g (5.5 mmol) sodium azide were stirred for 17 hours at room temperature under nitrogen atmosphere. 250 ml acetic acid and saturated sodium chloride solution were added to the reaction mixture. After mixing, the organic phase was removed and washed once with saturated sodium chloride solution and two times with water. The organic phase was dried with MgSO4 and the solvent was evaporated in a rotary evaporator at a temperature of the water-bath of 25° C. The obtained oil (0.40 g) was purified on silica gel ((60 Å, 60-200 µm) free flow agent: methylene chloride. 0.10 g (25% of the theoretical yield) of a orange-yellow solid material were obtained.

1H-NMR (CDCl3, 360 MHz): δ [ppm]=8.69 (mc, 2H), 8.57 (mc, 1H), 7.86 (mc, 2H), 7.47 (mc, 1H), 7.32 (mc, 2H), 3.42 (t, 2H), 2.72 (mc, 4H), 1.88 (mc, 4H), 1.13 (d, 12H).

As a by-product 0.10 g a compound was isolated which was the product of a cyclo-addition of the azido-residue with the hexinyl-residue.

1H-NMR (CDCl3, 360 MHz): δ [ppm]=8.91 (mc, 1H), 8.70 (mc, 2H), 7.76-7.86 (m, 2H), 7.47 (mc, 1H), 7.32 (mc, 2H), 4.56 (t, 2H), 2.94 (t, 2H), 2.77 (mc, 2H), 2.21 (mc, 2H), 2.00 (mc, 2H), 1.18 (d, 12H).

EXAMPLE 5

Synthesis of N-(2-sulfoethyl)-4-(6-azido-1-hexinyl)-naphthalene-1,8-dicarboxylic acid imide, sodium salt a) N-(2-Sulfoethyl)-naphthalene-1,8-dicarboxylic acid imide, potassium salt

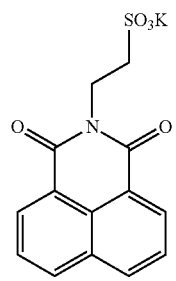

2.11 g (32.0 mmol) 85% KOH was dissolved in a solution of 5.01 g (40.0 mmol) 2-aminoethylsulfonic acid in 120 ml water. 1.98 g (10.0 mmol) 1,8-naphthaliene dicarboxylic acid was added to the solution. The solution was heated to 146° C. in a Roth reactor and stirred 3 hours at that temperature. The reactor was released after cooling to room temperature. The reaction mixture was filtrated. The residue was washed with a little water and dried. 2.84 g (83% of the theoretical yield) almost colorless solid were received.

1H-NMR (D2O, 360 MHz): δ [ppm]=8.06 (mc, 4H), 7.56 (mc, 2H), 4.23 (t, 2H), 3.16 (t, 2H).

b) N-(2-Sulfoethyl)-4-brom-naphthalene-1,8-dicarboxylic acid imide, sodium salt

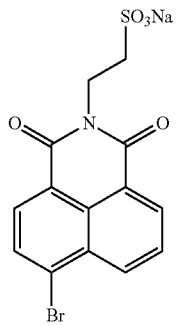

A solution of 0.91 g (2.96 mmol) N,N'-dibromo isocyanuric acid in 50 ml conc. sulfuric acid was added to a solution of 2.00 g (5.82 mmol) N-(2-sulfoethyl)-naphthalene-1,8-dicarboxylic acid imide, potassium salt, and 0.013 g (0,044 mmol) ferric(III) bromide in 100 ml conc. sulfuric acid within 2 hours at room temperature. The solution was stirred at room temperature overnight, then poured onto 500 g ice, and neutralized with NaOH. The solid was sucked off after adding 500 ml methanol, and washed with methanol. The filtrate was concentrated until 500 ml in the rotary evaporator, and then further concentrated to dryness in a vacuum drying cabinet at 75° C. The raw material was recrystallized from methanol. 1.28 g (46% of the theoretical yield) brownish solid were obtained. The compound crystallized with 4 water molecules according to the $^1$H-NMR-spectra.

1H-NMR (D6-DMSO, 500 MHz): δ [ppm]=8.76 (mc, 1H), 8.50 (mc, 1H), 8.45 (mc, 1H), 8.40 (mc, 1H), 7.90 (mc, 1H), 4.31 (t, 2H), 2.76 (t, 2H).

c) N-(2-Sulfoethyl)-4-(6-tosyloxy-1-hexinyl)-naphthalene-1,8-dicarboxylic acid imide, sodium salt

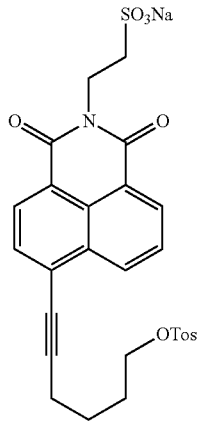

A solution of 0.91 g (3.60 mmol) p-toluene sulfonic acid 5-hexinylester (synthetized according to Y. Yang and T. M. Swager, Macromolecules 2006, 39, 2013-2015) in 40 ml dry degassed dimethylformamide (DMF) was added to a solution of 1.00 g (2.16 mmol) N-(2-sulfoethyl)-4-bromo-naphthalene-1,8-dicarboxylic acid imide, sodium salt, 0.27 g (1.68 mmol) copper iodide, 2.50 g (2.16 mmol) tetrakis(triphenylphosphin) palladium(0), and 0.49 g (0.48 mmol) triethylamine in 72 ml dry degassed DMF. The reaction solution was stirred for 70 hours at room temperature, and then concentrated to dryness in vacuum. The smeary residue was solidified by the addition of diethyl ether. The solid was sucked off, washed with diethyl ether, and dried. The raw material (3.08 g) was chromatographied by silica gel (60 Å, 60-200 μm) with toluene/methanol 2:1 as the eluent. 0.38 g (30% of the theoretical yield) brownish solid were obtained.

1H-NMR (D6-DMSO, 500 MHz): δ [ppm]=8.75 (mc, 1H), 8.47 (mc, 4H), 7.90 (mc, 2H), 7.47 (mc, 1H), 7.10 (mc, 1H), 4.32 (mc, 2H), 4.05 (mc, 2H), 2.77 (mc, 2H), 2.70 (mc, 2H), 2.29 (s, 3H), 1.80 (broad, 2H), 1.60 (broad, 2H).

d) N-(2-Sulfoethyl)-4-(6-azido-1-hexinyl)-naphthalene-1,8-dicarboxylic acid imide, sodium salt

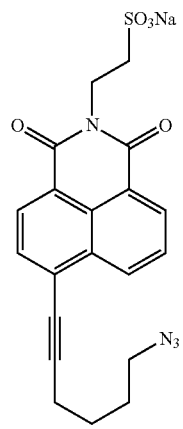

67 mg (0.14 mmol) hexadecyltributyl phosphonium azide (prepared according to K. Banert, Chem. Ber. 118, 1564-1574 (1985)) was added to a suspension of 51 mg (0,088 mmol) N-(2-sulfoethyl)-4-(6-tosyloxy-1-hexinyl)-naphthalene-1,8-dicarboxylic acid imide in 10 ml dry dimethylformamide. The conversion was complete after stirring for 21 hours at room temperature according to TLC. The residue was stirred each with 2 ml cyclohexane several times after the solvent had been removed in vacuum. The solid was sucked off, washed with cyclohexane, and was dried. 10 mg (25% of the theoretical yield) solid were obtained.

1H-NMR (D6-DMSO, 500 MHz): δ [ppm]=8.50 (mc, 1H), 8.47 (mc, 1H), 7.88 (mc, 1H), 7.49 (mc, 1H), 7.12 (mc, 1H), 4.32 (mc, 2H), 4.05 (mc, 2H), 2.78 (mc, 2H), 2.70 (mc, 2H), 2.58 (mc, 2H), 1.75-1.60 (breit, 4H). The peak of one methylene group could be hidden by the water peak at 3.48 ppm.

EXAMPLE 6

Click reaction of N-(2,6-diisopropylphenyl)-9-(6-azido-1-hexinyl)-perylene-3,4-dicarboxylic acid imide with alkinyl substituted DNA 150 μL of a 55 mM solution of N-(2,6-diisopropylphenyl)-9-(6-azido-1-hexinyl)-perylene-3,4-dicarboxylic acid imide in chloroform was added to 2.6 mg lyophilized alkinyl substituted DNA in a 15 mL Falcon tube. 300 mL of a 3:1 mixture of dimethylsulfoxid (DMSO) and tert.-butanol were added to the mixture and vortexed forming a two phase mixture. 20 μl of a 1 M buffer S solution made from 101.19 g triethylamine and 60.03 g acetic acid in 1 L water were added to the mixture and vortexed for 3 minutes. 100 μl of a 100 mM solution of copper bromide in a 3:1 mixture of DMSO and tert.-butanol and 200 μl of a 100 mM solution of tris(benzyltriazolylmethyl)amine (TBTA) in DMSO/tert.-butanol (3:1) were vortexed and added to the mixture containing the DNA. The reaction mixture appears now uniform and strongly red-colored. The solution was shaken at 25° C. for 22 hours. Then, 1 ml of a 0.3 M sodium acetate solution was added and the suspension was left standing for 1 hour with occasional vortexing. 8 mL of cold (−15° C.) absolute ethanol were added. The tube was then placed in a freezer (−20° C.) over night. After centrifugation (15 min at 13 000 rpm) the supernatant was carefully removed from the DNA pellet. 8 mL cold (−15° C.) ethanol were added, the vial vortexed, centrifuged and the supernatant removed. This washing step was repeated three times, then again three times using cold toluene instead of ethanol. After the last washing step the pellet was left drying on air, taken up in 2 mL water and used for preparative HPLC (from 0 to 40% buffer B in buffer A; buffer A=0.1 M buffer S in water, buffer B=0.1 M buffer S in acetonitrile).

Analysis of the fractions were done using MALDI-T of (Auto-Flex III, Bruker Daltonics) using hydroxypinacolic acid (HPA) as matrix.

The results are shown in FIG. 1.

All the references described above are incorporated by reference in their entirety for all useful purposes.

The invention claimed is:

1. A substituted naphthylene or rylene imide derivative of the general formula I

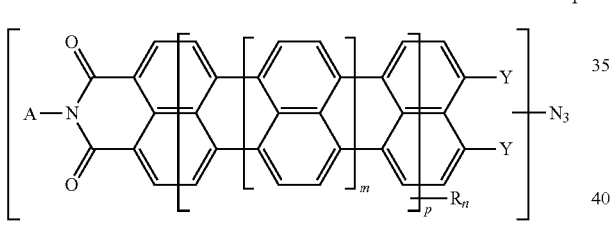

in which the variables are each defined as follows:
Y one of the two radicals is a radical of the formula (y2)

and the other radical in each case is hydrogen;
R are identical or different radicals:
aryloxy, arylthio, hetaryloxy or hetarylthio, to each of which may be fused further saturated or unsaturated 5- to 7-membered rings whose carbon skeleton may be interrupted by one or more —O—, —S—, —NR²—, —N=CR²—, —CO—, —SO— and/or —SO₂— moieties, where the entire ring system may be mono- or polysubstituted by the (i), (ii), (iii), (iv) and/or (v) radicals:
(i) $C_1$-$C_{30}$-alkyl whose carbon chain may be interrupted by one or more —O—, —S—, —NR²—, —N=CR²—, —CR²=CR²—, —CO—, —SO— and/or —SO₂— moieties and which may be mono- or polysubstituted by: $C_1$-$C_{12}$-alkoxy, $C_1$-$C_6$-alkylthio, —C☐CR², —CR²=CR²₂, hydroxyl, mercapto, halogen, cyano, nitro, —NR⁷R⁸, —NR³COR⁴, —CONR³R⁴, —SO₂NR³R⁴, —COOR⁵, —SO₃R⁵, —PR⁵₂, —POR⁵R⁵, (het)aryl and/or saturated or unsaturated $C_4$-$C_7$-cycloalkyl whose carbon skeleton may be interrupted by one or more —O—, —S—, —NR²—, —N=CR²—, —CR²=CR²—, —CO—, —SO— and/or —SO₂— moieties, where the (het)aryl and cycloalkyl radicals may each be mono- or polysubstituted by $C_1$-$C_{18}$-alkyl and/or the above radicals specified as substituents for alkyl;
(ii) $C_3$-$C_8$-cycloalkyl whose carbon skeleton may be interrupted by one or more —O—, —S—, —NR²—, —N=CR²—, —CR²=CR²—, —CO—, —SO— and/or —SO₂— moieties and to which may be fused further saturated or unsaturated 5- to 7-membered rings whose carbon skeleton may be interrupted by one or more —O—, —S—, —NR²—, —N=CR²—, —CR²=CR²—, —CO—, —SO— and/or —SO₂— moieties, where the entire ring system may be mono- or polysubstituted by: $C_1$-$C_{18}$-alkyl, $C_1$-$C_{12}$-alkoxy, $C_1$-$C_6$-alkylthio, —C=CR², —CR²=CR²₂, hydroxyl, mercapto, halogen, cyano, nitro, —NR⁷R⁸, —NR³COR⁴, —CONR³R⁴, —SO₂NR³R⁴, —COOR⁵, —SO₃R⁵, —PR⁵₂ and/or —POR⁵R⁵;
(iii) aryl or hetaryl to which may be fused further saturated or unsaturated 5- to 7-membered rings whose carbon skeleton may be interrupted by one or more —O—, —S—, —NR²—, —N=CR²—, —CR²=CR²—, —CO—, —SO— and/or —SO₂— moieties, where the entire ring system may be mono- or polysubstituted by: $C_1$-$C_{18}$-alkyl, $C_1$-$C_{12}$-alkoxy, $C_1$-$C_6$-alkylthio, —C=CR², —CR²=CR²₂, hydroxyl, mercapto, halogen, cyano, nitro, —NR⁷R⁸, —NR³COR⁴, —CONR³R⁴, —SO₂NR³R⁴, —COOR⁵, —SO₃R⁵, —PR⁵₂, —POR⁵R⁵, (het)aryl, (het)aryloxy and/or (het)arylthio, where the (het)aryl radicals may each be mono- or polysubstituted by $C_1$-$C_{18}$-alkyl, $C_1$-$C_{12}$-alkoxy, $C_1$-$C_6$-alkylthio, hydroxyl, mercapto, halogen, cyano, nitro, —NR⁷R⁸, —NR³COR⁴, —CONR³R⁴, —SO₂NR³R⁴, —COOR⁵, —SO₃R⁵, —PR⁵₂, —POR⁵R⁵;
(iv) a —U-aryl radical which may be mono- or polysubstituted by the above radicals specified as substituents for the aryl radicals (iii), where U is a —O—, —S—, —NR³—, —CO—, —SO— or —SO₂— moiety;
(v) $C_1$-$C_{12}$-alkoxy, $C_1$-$C_6$-alkylthio, —C=CR², —CR²=CR²₂, hydroxyl, mercapto, halogen, cyano, nitro, —NR⁷R⁸, —NR³COR⁴, —CONR³R⁴, —SO₂NR³R⁴, —COOR⁵, —SO₃R⁵, —PR⁵₂ and/or —POR⁵R⁵;
(vi) E-D-SO₃⁻, D is selected from the group of residues as depicted under (ii) and (iii), whereby the counterion of the anion (—SO₃⁻) respectively cation is selected from the group consisting of metal ion and quarternary ammonium ions L is a chemical bond or
an arylene or hetarylene radical, bonded to the rylene skeleton directly or via ethenylene or ethynylene, of the formulae —Ar—

—Ar-E-Ar— in which the (het)arylene radicals Ar may be the same or different, may comprise heteroatoms as ring atoms and/or may have fused saturated or unsaturated 5- to 7-membered rings which may likewise comprise heteroatoms, where the entire ring system may be mono- or polysubstituted by phenyl, $C_1$-$C_{12}$-alkyl, $C_1$-$C_{12}$-alkoxy, $C_1$-$C_{12}$-alkylthio and/or —NR³R⁴;

E is a chemical bond or an —O—, —S—, —NR$^2$—, —C≡C—, —CR$^2$=CR$^2$— or $C_1$-$C_6$-alkylene moiety;

Z is —O— or —S— or a carbon-carbon single, double or triple bond, provided that L and Z are not simultaneously a chemical bond;

R$^1$ is one of the alkyl radicals (i) or (het)aryl radicals (iii) specified as substituents for the R radicals;

A is:
  hydrogen;
  $C_1$-$C_{30}$-alkyl whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties and which may be mono- or polysubstituted by the (ii), (iii), (iv) and/or (v) radicals specified as substituents for the R radicals;
  $C_3$-$C_8$-cycloalkyl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by the (i), (ii), (iii), (iv) and/or (v) radicals specified as substituents for the R radicals;
  aryl or hetaryl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by the (i), (ii), (iii), (iv), (v) radicals specified as substituents for the R radicals, and/or aryl- and/or hetarylazo, each of which may be substituted by $C_1$-$C_{10}$-alkyl, $C_1$-$C_6$-alkoxy and/or cyano;
  E-D-SO$_3^-$, D is selected from the group of residues as depicted under (ii) and (iii), whereby the counterion of the anion (—SO$_3^-$) respectively cation is selected from the group consisting of metal ion and quarternary ammonium ions, R$^2$ is hydrogen or $C_1$-$C_{18}$-alkyl, where the R$^2$ radicals may be the same or different when they occur more than once;

R$^3$, R$^4$ are each independently:
  hydrogen;
  $C_1$-$C_{18}$-alkyl whose carbon chain may be interrupted by one or more —O—, —S—, —CO—, —SO—and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^6$;
  aryl or hetaryl to each of which may be fused further saturated or unsaturated 5- to 7-membered rings whose carbon skeleton may be interrupted by one or more —O—, —S—, —CO—and/or —SO$_2$— moieties, where the entire ring system may be mono- or polysubstituted by $C_1$-$C_{12}$-alkyl and/or the above radicals specified as substituents for alkyl;
  where the R$^3$ radicals may be the same or different when they occur more than once;

R$^5$ is hydrogen, a $C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^6$;
  aryl or hetaryl to each of which may be fused further saturated or unsaturated 5- to 7-membered rings whose carbon skeleton may be interrupted by one or more —O—, —S—, —CO—and/or —SO$_2$— moieties, where the entire ring system may be mono- or polysubstituted by $C_1$-$C_{12}$-alkyl and/or the above radicals specified as substituents for alkyl, where the R$^5$ radicals may be the same or different when they occur more than once;

R$^6$ is $C_1$-$C_{18}$-alkyl;

R$^7$, R$^8$ are each $C_1$-$C_{30}$-alkyl whose carbon chain may be interrupted by one or more —O—, —S—, —NR$^2$—, —N=CR$^2$—, —C≡C—, —CR$^2$=CR$^2$—, —CO—, —SO— and/or —SO$_2$— moieties and which may be mono- or polysubstituted by: $C_1$-$C_{12}$-alkoxy, $C_1$-$C_6$-alkylthio, —C≡CR$^2$, —CR$^2$=CR$^2{}_2$, hydroxyl, —NR$^3$R$^4$, —NR$^3$COR$^4$, (het)aryl and/or saturated or unsaturated $C_4$-$C_7$-cycloalkyl whose carbon skeleton may be interrupted by one or more —O—, —S—, —NR$^2$—, —N=CR$^2$— and/or —CR$^2$=CR$^2$ moieties, where the (het)aryl and cycloalkyl
  radicals may each be mono- or polysubstituted by $C_1$-$C_{18}$-alkyl and/or the above radicals specified as substituents for alkyl;
  aryl or hetaryl to which may be fused further saturated or unsaturated 5- to 7-membered rings whose carbon skeleton may be interrupted by one or more —O—, —S—, —NR$^2$—, —N=CR$^2$—, —CR$^2$=CR$^2$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^2$, —CR$^2$=CR$^2{}_2$, hydroxyl, —NR$^3$R$^4$, —NR$^3$COR$^4$, (het)aryl, (het)aryloxy and/or (het)arylthio, where the (het)aryl radicals may in each case be mono- or
  polysubstituted by $C_1$-$C_{18}$-alkyl, $C_1$-$C_{12}$-alkoxy, hydroxyl, —NR$^3$R$^4$ and/or —NR$^3$COR$^4$;
  joined to the nitrogen atom to form a saturated or unsaturated, 5- to 7-membered ring whose carbon chain may be interrupted by one or more —O—, —S— and/or —NR$^2$— moieties, to which may be fused one or two unsaturated or saturated 4- to 8-membered rings whose carbon chain may likewise be interrupted by these moieties and/or —N=, where the entire ring system may be mono- or polysubstituted by $C_1$-$C_{24}$-alkyl which may be substituted by $C_1$-$C_{18}$-alkoxy, $C_1$-$C_{18}$-alkylthio and/or —NR$^3$R$^4$, (het)aryl which may be mono- or polysubstituted by $C_1$-$C_{18}$-alkyl and/or the above radicals specified as substituents for alkyl, $C_1$-$C_{18}$-alkoxy, $C_1$-$C_{18}$-alkylthio and/or —NR$^3$R$^4$;

m is 0;

n is an integer in the range of from 0 to 6; and p is 1.

2. The substituted naphthylene or rylene-imide derivative according to claim 1 having the formula Ic

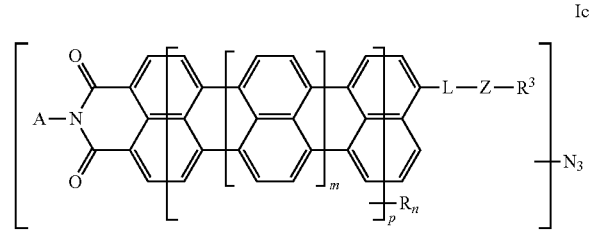

wherein A and R are as defined in claim 1.

3. The substituted naphthylene or rylene imide derivative in accordance with claim 1, wherein A has the following meaning

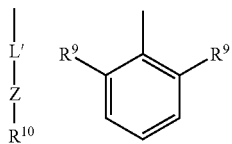

where the variables are each defined as follows:
$R^9$ is $C_3$-$C_8$-alkyl with a secondary carbon atom in the 1-position;
$R^{10}$ is phenyl, when L' is a chemical bond;
  $C_4$-$C_{18}$-alkyl when L' is 1,4-phenylene or a chemical bond;
L' is a chemical bond, 1,4-phenylene or 2,5-thienylene;
Z is —O— or —S— or a carbon-carbon single, double or triple bond, provided that L' and Z are not simultaneously a chemical bond.

4. The substituted naphthylene or rylene imide derivative in accordance with claim 2, wherein A has the following meaning

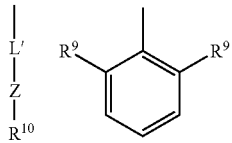

where the variables are each defined as follows:
$R^9$ is $C_3$-$C_8$-alkyl with a secondary carbon atom in the 1-position;
$R^{10}$ is phenyl, when L' is a chemical bond;
  $C_4$-$C_{18}$-alkyl when L' is 1,4-phenylene or a chemical bond;
L' is a chemical bond, 1,4-phenylene or 2,5-thienylene;
Z is —O— or —S— or a carbon-carbon single, double or triple bond, provided that L' and Z are not simultaneously a chemical bond.

5. The substituted naphthylene or rylene-imide derivative according to claim 1 wherein the rylene skeleton has the formula (I9) or (I10)

I9

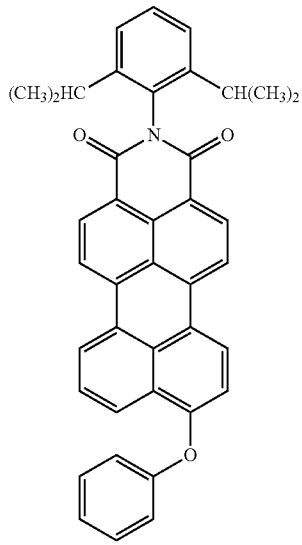

I10

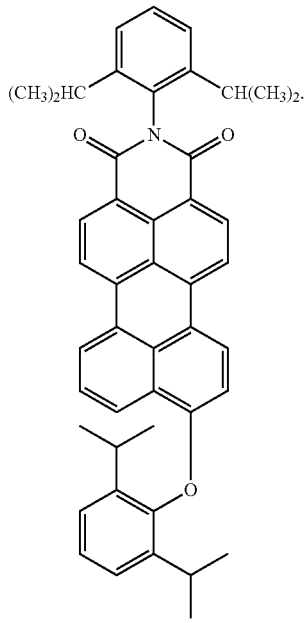

6. A reagent kit for detecting an analyte in a sample, comprising:
(a) a functionalized compound comprising at least one functional group which is a first reaction partner for a click reaction,
(b) a second reaction partner for a click reaction, wherein the second reaction partner further comprises a marker group said second reaction partner being selected from the mono-azide substituted naphthylene or rylene-imide derivative in accordance with claim 1.

7. A method for detecting an analyte comprising the steps of
(i) providing a sample;
(ii) contacting the sample with a functionalized compound comprising at least one functional group which is a first reaction partner for a click reaction under conditions wherein said compound forms an association product with the analyte to be detected,
(iii) contacting the association product with a second reaction partner for a click reaction under conditions wherein a click reaction between the first and second reaction partner occurs, wherein the second reaction partner is a mono-azide substituted naphthylene or rylene-imide derivative in accordance with claim 1, and
(iv) detecting the marker groups in the compounds in the mono-azide substituted naphthylene or rylene-imide derivative in accordance with claim 1.

* * * * *